US006317617B1

(12) United States Patent
Gilhuijs et al.

(10) Patent No.: US 6,317,617 B1
(45) Date of Patent: *Nov. 13, 2001

(54) METHOD, COMPUTER PROGRAM PRODUCT, AND SYSTEM FOR THE AUTOMATED ANALYSIS OF LESIONS IN MAGNETIC RESONANCE, MAMMOGRAM AND ULTRASOUND IMAGES

(75) Inventors: Kenneth Gilhuijs, Chicago; Maryellen L. Giger, Elmhurst; Ulrich Bick, Chicago, all of IL (US)

(73) Assignee: Arch Development Corporation, Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/900,188

(22) Filed: Jul. 25, 1997

(51) Int. Cl.[7] ..................................... A61B 5/00
(52) U.S. Cl. ................... 600/408; 600/411; 600/420; 600/427; 600/431; 600/443; 600/458; 128/922; 382/131; 706/20
(58) Field of Search .................... 128/920, 922; 600/407, 408, 410, 411, 420, 425, 427, 431, 437, 443, 458; 706/15, 20, 21; 382/128, 131, 132

(56) References Cited

U.S. PATENT DOCUMENTS

| 4,907,156 |   | 3/1990  | Doi et al. .           |
|-----------|---|---------|------------------------|
| 5,059,415 | * | 10/1991 | Neuwelt ......... 600/420 |
| 5,133,020 |   | 7/1992  | Giger et al. .         |
| 5,235,510 | * | 8/1993  | Yamada et al. ... 600/407 |
| 5,279,301 | * | 1/1994  | Tsukaya et al. ... 600/442 |
| 5,415,163 | * | 5/1995  | Harms et al. ..... 600/420 |
| 5,452,367 |   | 9/1995  | Bick et al. .          |
| 5,463,548 | * | 10/1995 | Asada et al. ..... 600/300 |
| 5,537,485 |   | 7/1996  | Nishikawa et al. .     |
| 5,638,458 |   | 6/1997  | Giger et al. .         |
| 5,657,362 |   | 8/1997  | Giger et al. .         |

* cited by examiner

Primary Examiner—Ruth S. Smith
(74) Attorney, Agent, or Firm—Oblon, Spivak, McClelland, Maier & Neustadt, P.C.

(57) ABSTRACT

A method and system for the computerized automatic analysis of lesions in magnetic resonance (MR) images, a computer programmed to implement the method, and a data structure for storing required parameters is described. Specifically the system includes the computerized analysis of lesions in the breast using spatial, temporal and/or hybrid measures. Techniques include novel developments and implementations of two-dimensional and three-dimensional features to assess the characteristics of the lesions and in some cases give an estimate of the likelihood of malignancy or of prognosis. The system can also allow for the enhanced visualization of the breast and its pathological states. The system also includes an option to merge the extracted features with those from x-ray and/or ultrasound images in order to further characterize the lesion and/or make a diagnosis and/or a prognosis.

51 Claims, 22 Drawing Sheets

METHOD, COMPUTER PROGRAM PRODUCT, AND SYSTEM FOR THE AUTOMATED ANALYSIS OF LESIONS IN MAGNETIC RESONANCE, MAMMOGRAM AND ULTRASOUND IMAGES

CROSS REFERENCES TO RELATED APPLICATIONS

The present invention generally relates to CAD techniques for automated detection of abnormalities in digital images, for example, as disclosed in one or more of U.S. Pat. Nos. 4,839,807; 4,841,555; 4,851,984; 4,875,165; 4,907,156; 4,918,534; 5,072,384; 5,133,020; 5,150,292; 5,224,177; 5,289,374; 5,319,549; 5,343,390; 5,359,513; 5,452,367; 5,463,548; 5,491,627; 5,537,485; 5,598,481; 5,622,171; 5,638,458; 5,657,362; 5,666,434; 5,673,332; 5,668,888; and 5,740,268; as well as U.S. patent applications 08/158,388; 08/173,935; 08/220,917; 08/398,307; 08/428,867; 08/523,210; 08/536,149; 08/536,450; 08/515,798; 08/562,087; 08/757,611; 08/758,438; 08/900,191; 08/900,192; and 08/900,189, all of which are incorporated herein by reference.

The present invention includes use of various technologies referenced and described in the above-noted U.S. Patents and Applications, as well as described in the references identified in the following LIST OF REFERENCES by the author(s) and year of publication and cross-referenced throughout the specification by reference to the respective number, in parentheses, of the reference:

LIST OF REFERENCES (1) American Cancer Society: *Cancer Facts and Figures—1995*. Atlanta: American Cancer Society, 1995.
(2) Feig S A: Decreased breast cancer mortality through mammographic screening: Results of clinical trials. *Radiology* 167:659–665, 1988.
(3) Tabar L, Fagerberg G, Duffy S W, Day N E, Gad A, Grontoft O: Update of the Swedish two-county program of mammographic screening for breast cancer. *Radiol. Clin. North Am.* 30:187–210, 1992.
(4) Smart C R, Hendrick R E, Rutledge J H, Smith R A: Benefit of mammography screening in women ages 40 to 49 years: Current evidence from randomized controlled trials. *Cancer* 75:1619–26, 1995.
(5) Bassett L W, Gold R H: *Breast Cancer Detection: Mammography and Other Methods in Breast Imaging* New York: Grune and Stratton, 1987.
(6) Kopans D B: *Breast Imaging*. Philadelphia: J B Lippincott, 1989.
(7) Brown M L, Houn F, Sickles E A, Kessler L G: Screening mammography in community practice: positive predictive value of abnormal findings and yield of follow-up diagnostic procedures. *AJR* 165:1373–1377, 1995.
(8) Jackson V P: The role of US in breast imaging. *Radiology* 177:305–311, 1990.
(9) Hilton S W, Leopold G R, Olson L K, Wilson S A: Real-time breast sonography: application in 300 consecutive patients. *AJR* 147:479–486, 1986.
(10) Tohno E, Cosgrove D O, Sloane J P: *Ultrasound Diagnosis of Breast Diseases*. Churchill Livingstone, Edinburgh, 1994, pp. 50–73.
(11) Fornage B D, Lorigan J G, Andry E: Fibroadenoma of the breast: sonographic appearance. *Radiology* 172:671–675, 1989.
(12) Stavros A T, Thickman D, Rapp C L, Dennis M A, Parker S H, Sisney G A: Solid breast nodules: use of sonography to distinguish between benign and malignant lesions. *Radiology* 196:123–134, 1995.
(13) Muller-Schimpfle M, Stoll P, Stern W. et al.: Do mammography, sonography, and MR mammography have a diagnostic benefit compared with mammography and sonography? *AJR* 168: 1323–1329, 1997.
(14) Brinck U, Fischer U, Korabiowska M, et al.: The variability of fibroadenoma in contrast-enhanced dynamic MR mammography. *AJR* 168:1331–1334, 1997.
(15) Adams A H, Brookeman J R, Merickel M B: Breast lesion discrimination using statistical analysis and shape measures on magnetic resonance imagery. *Comp. Med. Imaging and Graphics* 15: 339–349, 1991.
(16) Huber S, Delorme S, Knopp M V, Junkermann H, Zuna I, von Fournier D, van Kaick G: Breast tumors: computer-assisted quantitative assessment with color Doppler US. *Radiology* 192:797–801, 1994.
(17) Giger M L: Computer-aided diagnosis. In: *Syllabus: A Categorical Course on the Technical Aspects of Breast Imaging*, edited by Haus A, Yaffe M. Oak Brook, I L: RSNA Publications, 1993, pp. 272–298.
(18) Vyborny C J, Giger M L: Computer vision and artificial intelligence in mammography. *AJR* 162:699–708, 1994.
(19) Gale A G, Roebuck E J, Riley P, Worthington B S, et al.: Computer aids to mammographic diagnosis. *British Journal of Radiology* 60: 887–891, 1987.
(20) Getty D J, Pickett R M, D'Orsi C J, Swets J A: Enhanced interpretation of diagnostic images. *Invest. Radiol* 23: 240–252, 1988.
(21) Swett H A, Miller P A: ICON: A computer-based approach to differential diagnosis in radiology. *Radiology* 163: 555–558, 1987.
(22) Huo Z, Giger M L, Vybomy C J, Bick U, Lu P, Wolverton D E, Schmidt R A: Analysis of spiculation in the computerized classification of mammographic masses. *Medical Physics* 22:1569–1579, 1995.
(23) Jiang Y, Nishikawa R M, Wolverton D E, Giger M L, Doi K, Schmidt R A, Vybomy C J: Automated feature analysis and classification of malignant and benign clustered microcalcifications. *Radiology* 198(3):671–678, 1996.
(24) Chan H P, Doi K, Galhotra S, Vybomy C J, MacMahon H, Jokich P M: Image feature analysis and computer-aided diagnosis in digital radiography. 1. Automated detection of microcalcifications in mammography. *Medical Physics* 14: 538–548, 1987.
(25) Chan H P, Doi K, Vyborny C J, Lam K L, Schmidt R A: Computer-aided detection of microcalcifications in mammograms: Methodology and preliminary clinical study. *Invest. Radiol* 23: 664–671, 1988.
(26) Chan H P, Doi K, Vyborny C J, Schmidt R A, Metz C E, Lam K L, Ogura T, Wu Y, MacMahon H: Improvement in radiologists' detection of clustered microcalcifications on mammograms: The Potential of computer-aided diagnosis. *Invest. Radiol.* 25: 1102–1110, 1990.
(27) Nishikawa R M, Doi K, Giger M L, Yoshimura H, Wu Y, Vybomy C J, Schmidt R A, Chan H P: Use of morphological filters in the computerized detection of microcalcifications in digital mammograms. *Medical Physics* 17: 524, 1990.
(28) Nishikawa R M, Giger M L, Doi K, Vybomy C J, Schmidt R A: Computer-aided detection of clustered microcalcifications: An improved method for grouping detected signals. *Medical Phys* 20: 1661–1666, 1993.
(29) Giger M L, Yin F-F, Doi K, Metz C E, Schmidt R A, Vyborny C J: Investigation of methods for the computerized detection and analysis of mammographic masses. *Proc. SPIE* 1233: 183–184, 1990.

(30) Yin F-F, Giger M L, Doi K, Metz C E, Vyborny C J, Schmidt R A: Computerized detection of masses in digital mammograms: Analysis of bilateral-subtraction images. *Medical Physics* 18: 955–963, 1991.

(31) Yin F F, Giger M L, Vyborny C J, Doi K, Schmidt R A: Comparison of bilateral-subtraction and single-image processing techniques in the computerized detection of mammographic masses. *Invest. Radiol* 28: 473–481, 1993.

(32) Yin F F, Giger M L, Doi K, Vybomy C J, Schmidt R A: Computerized detection of masses in digital mammograms: Investigation of feature-analysis techniques. *Journal of Digital Imaging* 7:18–26, 1994.

(33) Yin F F, Giger M L, Doi K, Vyborny C J, Schmidt R A: Computerized detection of masses in digital mammograms: Automated alignment of breast images and its effect on bilateral-subtraction technique. *Med Phys* 21:445–452, 1994.

(34) Nishikawa R M, Giger M L, Doi K, Vybomy C J, Schmidt R A; Computer-aided detection of clustered microcalcifications on digital mammograms. *Medical and Biological Engineering and Computing* 33:174–178, 1995.

(35) Bick U, Giger M L, Huo Z, Schmidt R A, Doi K, Nishikawa R M, Vyborny C J: Automated detection of skin thickening in mammograms. *Proc. CAR '93* pgs. 461–465, 1993.

(36) Bick U, Giger M L, Schmidt R A, Nishikawa R M, Wolverton D E , Lu P, Vyborny C J, Doi K: Automated segmentation of digitized mammograms. *Academic Radiology* 2: 1–9, 1995.

(37) Zhang W, Doi K, Giger M L, Wu Y, Nishikawa R M, Schmidt R A: Computerized detection of clustered microcalcifications in digital mammograms using a shift-invariant artificial neural network. *Med Phys* 21:517–524, 1994.

(38) Bick U, Giger M L, et al: A new single-image method for computer-aided detection of small mammographic masses. *Proc. CAR '95*, Lemke H U, Inamura K, Jaffe C C, Vannier M W, eds. pgs. 357–363, 1995.

(39) Zhang M, Giger M L: Automated detection of spiculated lesions mid architectural distortions in digitized mammograms. *Proc SPIE* 2434: 846–854, 1995.

(40) Kupinski M, Giger M L, Lu P, Huo Z: Computerized detection of mammographic lesions: Performance of artificial neural network with enhanced feature extraction. *Proc SPIE* 2434:598–605, 1995.

(41) Giger M L, Nishikawa R M, Doi K, Yin F F, Vyborny C J, Schmidt R A, Metz C E, Wu Y, MacMahon H, Yoshimura H: Development of a "smart" workstation for use in mammography. *Proc. SPIE* 1445: 101–103, 1991.

(42) Doi K, Giger M L, MacMahon H, Hoffmann K R, et al.: Computer-aided diagnosis: development of automated schemes for quantitative analysis of radiographic images. *Seminars in Ultrasound, C T and M R* 13: 140–152, 1992.

(43) Giger M L, Doi K, MacMahon H, Nishikawa R M, Hoffmann K R, et al.: An "intelligent" workstation for computer-aided diagnosis". *RadioGraphics* 13: 647–656, 1993.

(44) Nishikawa R M, Haldemann R C, Papaioannou J, Giger M L, Lu P, Schmidt R A, Wolverton D E , Bick U, Doi K: Initial experience with a prototype clinical "intelligent" mammography workstation for computer-aided diagnosis. *Proc SPIE* 2434–65–71, 1995.

(45) Giger M L, Vyborny C J, Schmidt R A: Computerized characterization of mammographic masses: Analysis of spiculation. *Cancer Letters* 77: 201–211, 1994.

(46) Wu Y, Doi K, Giger M L, Nishikawa R M: Computerized detection of clustered microcalcifications in digital mammograms: applications of artificial neural networks. *Radiology* 19: 555–560, 1992.

(47) Wu Y, Giger M L, Doi K, Vybomy C J, Schmidt R A, Metz C E: Application of neural networks in mammography: Applications in decision making in the diagnosis of breast cancer. *Radiology* 187: 81–87, 1993.

(48) Metz C E: Some practical issues of experimental design and data analysis in radiologicalROC studies. *Invest. Radiol.* 24: 234–245, 1989.

(49) Bamber D: The area above the ordinal dominance graph and the area below the receiver operating graph. *J Math Psych* 12: 387–415, 1975.

(50) Kupinski M, Giger M L, Doi K: Optimization of neural network inputs with genetic algorithms. Digital Mammography '96. Proceedings of the 3rd International Workshop of Digital Mammography, Elsevier, New York, pp. 401–404, 1996.

The entire contents of each related patent and application listed above and each reference listed in the LIST OF REFERENCES, are incorporated herein by reference.

This invention was made in part with U.S. Government support under USPHS grants AR 43439 and RR 11459 and U.S. Army grant DAMD17-96-1-6058. The Government has certain rights in the invention.

BACKGROUND OF THE INVENTION

1. Field of the Invention

The invention relates generally to a method and system for the computerized automatic analysis of lesions in magnetic resonance images. Specifically the system includes the computerized analysis of lesions in the breast using both two-dimensional and three-dimensional analyses. Techniques of the present invention include novel developments and implementations of spatial, temporal, and hybrid features to assess the characteristics of the lesions and in some cases give an estimate of the likelihood of malignancy or of prognosis, and also allow for the enhanced visualization of the breast and its pathological states. The system of the present invention also includes an option to merge the extracted features with those from x-ray and/or ultrasound images in order to further characterize the lesion and/or make a diagnosis and/or a prognosis.

2. Discussion of Background

Breast cancer is a leading cause of death in women, causing an estimated 46,000 deaths per year. (See Reference (1)). Mammography is the most effective method for the early detection of breast cancer, and it has been shown that periodic screening of asymptomatic women does reduce mortality. (See References (2)–(4)). Many breast cancers are detected and referred for surgical biopsy on the basis of a radiographically detected mass lesion or cluster of microcalcifications. Although general rules for the differentiation between benign and malignant mammographically identified breast lesions exist (see references (5)–(6)), considerable misclassification of lesions occurs with the current methods. On average, less than 30% of masses referred for surgical breast biopsy are actually malignant. (See reference (7)).

Breast MR imaging as an adjunct to mammography and sonography reveals breast cancer with a higher sensitivity than do mammography and sonography only. (See reference (13)). However, using all three methods in the human interpretation process yielded a lower specificity. It also has been shown that temporal analysis from dynamic MR correlates with intensity of fibrosis in fibroadenomas (see reference (14)). Some computerized analyses of spatial features are being performed. Adams et al. achieved a separation between malignant and benign lesions using a statistical analysis, however, their database consisted of only 16 cases. (See Reference (15)).

Computerized image analysis techniques that can objectively and reliably classify lesions based upon reported MR characteristics of benign and malignant masses, especially if combined with their mammographic features, could significantly improve the specificity of breast imaging and the evaluation of breast masses. Computer-aided techniques have been applied to the color Doppler evaluation of breast masses with promising results. (See reference (16)). However, color Doppler imaging is a technique which focuses only upon the vascularity of lesions. Since not all sonographically visible cancers have demonstrable neovascularity, this technique is inherently somewhat limited. On the other hand, computer-aided diagnosis techniques applied to gray-scale sonographic images has not yet been reported. In addition, computerized analysis of MR images of the breast has mainly been limited to only temporal analysis using contrast media.

Comprehensive summaries of investigations in the field of mammography CAD have been published. (See references (17)–(18)). In the 1960s and 70s, several investigators attempted to analyze mammographic abnormalities with computers. These previous studies demonstrated the potential capability of using a computer in the detection of mammographic abnormalities. Gale et al. (see reference (19)) and Getty et al. (see reference (20)) are both developing computer-based classifiers, which take as input diagnostically-relevant features obtained from radiologists' readings of breast images. Getty et al. found that with the aid of the classifier, community radiologists performed as well as unaided expert mammographers in making benign-malignant decisions. Swett et al. (see reference (21)) are developing an expert system to provide visual and cognitive feedback to the radiologist using a critiquing approach combined with an expert system. At the University of Chicago, we have shown that the computerized analysis of mass lesions (see reference (22)) and clustered microcalcifications (see reference (23)) on digitized mammograms yields performances similar to an expert mammographer and significantly better than average radiologists in the task of distinguishing between malignant and benign lesions.

SUMMARY OF THE INVENTION

Accordingly, an object of this invention is to provide a method and system for the analysis of lesions in magnetic resonance (MR) images.

Another object of this invention is to provide an automated method and system for the characterization of lesions using computer-extracted features from MR images of the breast.

Another object of this invention is to provide an automated method and system for determination of spatial features to assess the characteristics of the lesions in MR images.

A further object of this invention is to provide an automated method and system for determination of temporal features to assess the characteristics of the lesions in MR images.

A still further object of this invention is to provide an automated method and system for determination of hybrid features to assess the characteristics of the lesions in MR images.

An additional object of this invention is to provide an automated method and system for merging computer-extracted information from mammographic, ultrasound, and/or MR images and making a diagnosis and/or prognosis.

A further object of the invention is to provide an automated method and system for determining an estimate of the likelihood of malignancy or of prognosis of a lesion on an MR image.

Yet another object of the invention is to provide a method and system for presenting an enhanced visualization of the breast from a medical image.

The above and other objects are achieved according to the present invention by providing a new and improved method for the analysis of lesions in magnetic resonance (MR) images, including generating MR image data from the MR images; and extracting features that characterize a lesion within the MR image data, including extracting at least one of temporal, spatial, and hybrid features of the lesion.

BRIEF DESCRIPTION OF THE DRAWINGS

A more complete appreciation of the invention and many of the attendant advantages thereof will be readily obtained as the same becomes better understood by reference to the following detailed descriptions when considered in connection with the accompanying drawings, wherein.

DESCRIPTION OF THE PREFERRED EMBODIMENTS

Figure 1A:
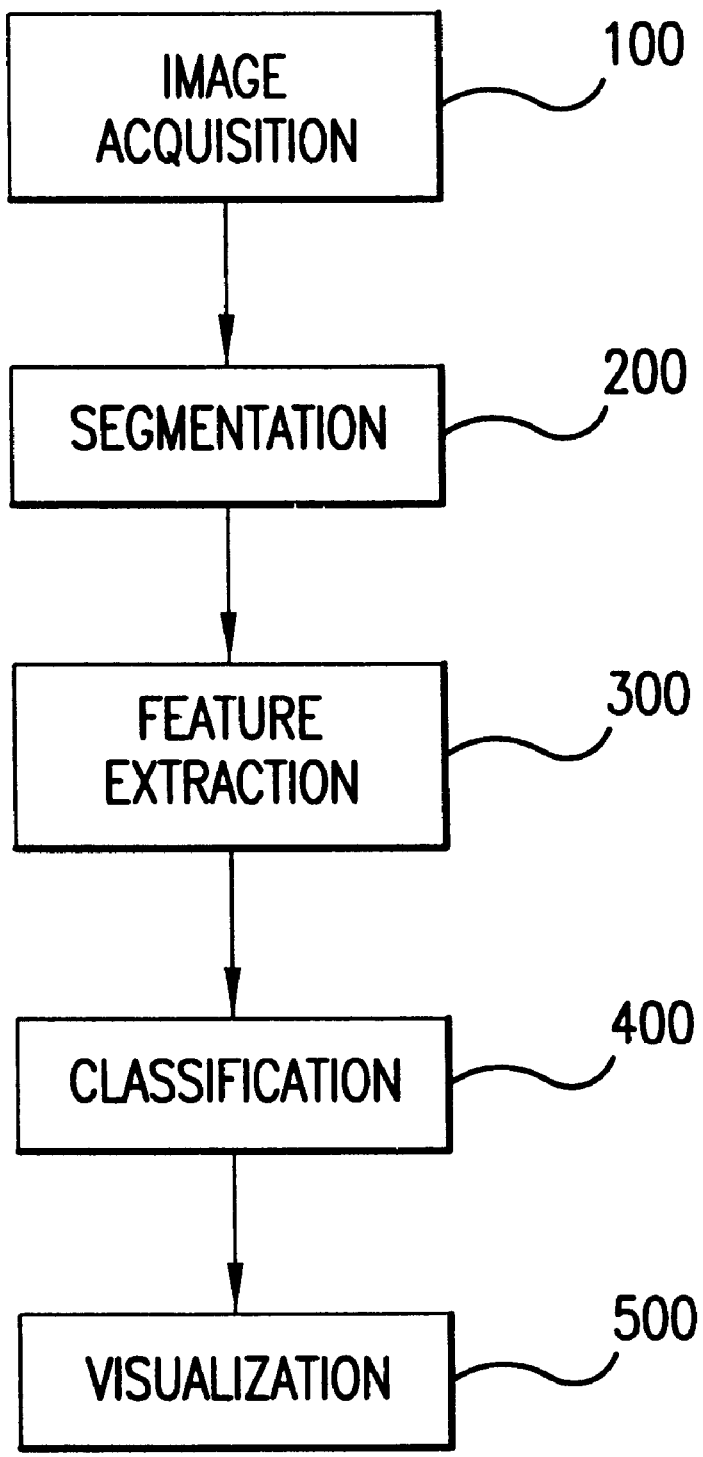
FIG. 1A is a flow chart of the method for the automated analysis of lesions in MRI images, which consists of five consecutive stages: MRI image acquisition, segmentation to identify the regions of interest, feature extraction to compute properties from these regions of interest, classification to combine the different features into an estimate of malignancy, and visualization for assessment of lesion size, shape and location with respect to known landmarks, according to the present invention.

Referring now to the drawings, wherein like reference numerals designate identical or corresponding parts throughout the several views, and more particularly to FIG. 1A thereof, there is shown a flow chart illustrating the automated method for the analysis and characterization of lesions in MR images according to the present invention. In FIG. 1A, an initial acquisition of a set of MR images that comprise a volume, and presentation of the images in digital format is performed (step 100). The image analysis scheme consists of four consecutive stages: segmentation of the breast and lesions (step 200), the spatial, temporal, and/or hybrid feature extraction (step 300), the rule-based, analytic, and/or artificial neural network (ANN) classification (step 400), and the volume rendering, surface rendering, wire framing, and/or voxel modification visualization (step 500), the details of which will be described later.

Figure 1B:
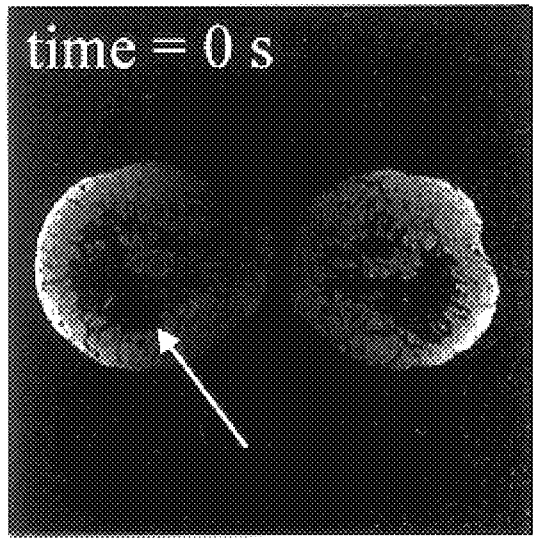
FIG. 1B is an example of a dynamic MR sequence of a malignant lesion.
Figure 1C:
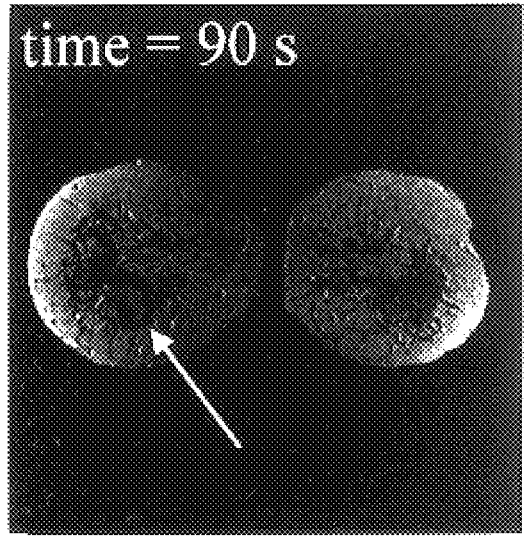
FIG. 1C is a methods overview for characterizing a lesion in an MR image in order to determine a likelihood of malignancy, according to the present invention.
Figure 1D:
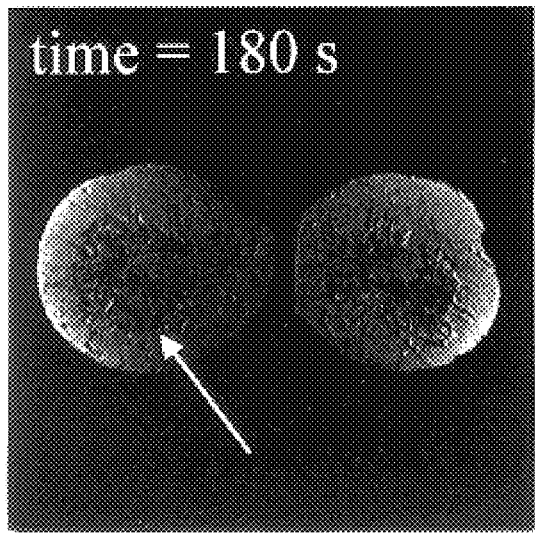
FIG. 1D is a display of a lesion in 3-D, wherein all features are analyzed in either 2-D, 3-D, and/or both, according to the present invention.
Figure 2:
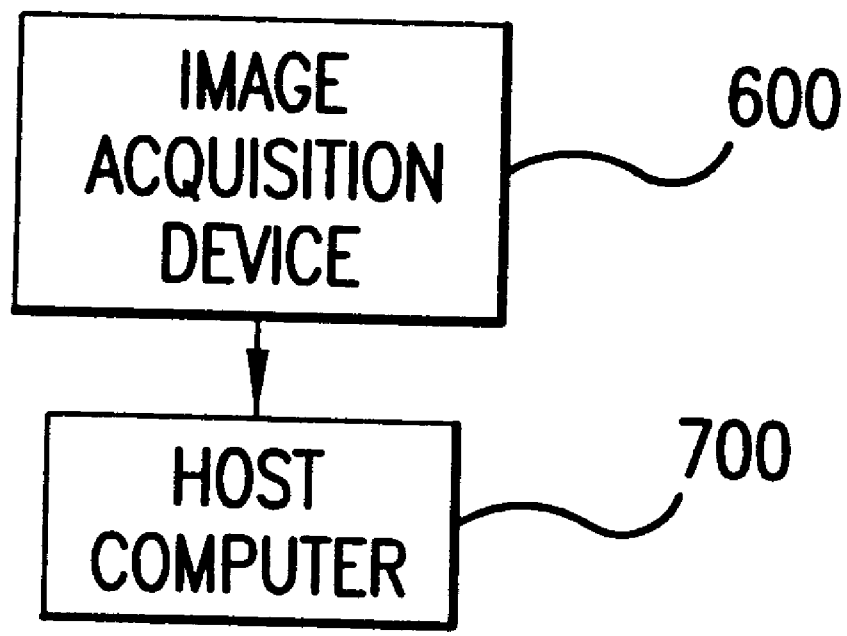
FIG. 2 is a system diagram of the system for the automated analysis of lesions in MRI images, according to the present invention.

FIG. 1B shows an example of a dynamic MR sequence of a malignant lesion, for example, as acquired in the image acquisition (step 100, FIG. 1A) by the image acquisition device 600 (FIG. 2). FIG. 1C shows a methods overview for characterizing a lesion in an MR image in order to determine a likelihood of malignancy. In FIG. 1C, an MR scan is performed at various time internals $t_0$ to $t_n$ to extract 3-D image of the lesion and to calculate spacial and temporal features used for discriminant analysis, to determine a likelihood of malignancy, diagnosis, and/or prognosis. In FIG. 1D, a lesion is displayed and analyzed in 3-D, according to the present invention.

Mammograms yield high spatial resolution images containing information on the structure of the lesion. Information on the spiculation and margin sharpness of the lesion can be extracted by extracting the lesion structure or by analysis (such as gradient analysis) of the immediate surround of a roughly-extracted lesion. In addition, the denseness of a lesion can be obtained from the amount of attenuation by the x-ray beam relative to the surround.

Ultrasound images of the breast yield information on the interior of the lesion (echonicity) as well as the interface between the lesion and its surround. Thus ultrasound is useful in distinguishing between solid lesions and fluid-filled lesions. Gradient analysis of the margins yields information on the interface between the lesion and the surround. Geometric measures relating the depth to the width of the lesion is useful in that although some lesions may be ellipsoid, the orientation of the ellipse is important in distinguishing among lesions. In addition, such features are useful in discriminating between solid benign lesions (such as a fibroadenoma) and a malignant lesion, when both may contain similar interior echonicity textures. Computerized analysis also allows for the objective assessment of posterior shadowing and posterior enhancement which aids in distinguishing between complex cysts and other lesions.

MR images of the breast can be analyzed to yield both structural and functional information of the lesion. By use of contrast medium, temporal information on the uptake by the lesion can be obtained yielding information on the vascularity of the lesion. Malignant lesions exhibit different amounts and patterns of vascularity than do benign lesions. Thus, in order to obtain maximum discriminating abilities, the merging of features from more than one modality is expected to improve the classification and characterization of lesions, and thus improve methods of diagnosis and assessing prognosis.

Figure 1E:
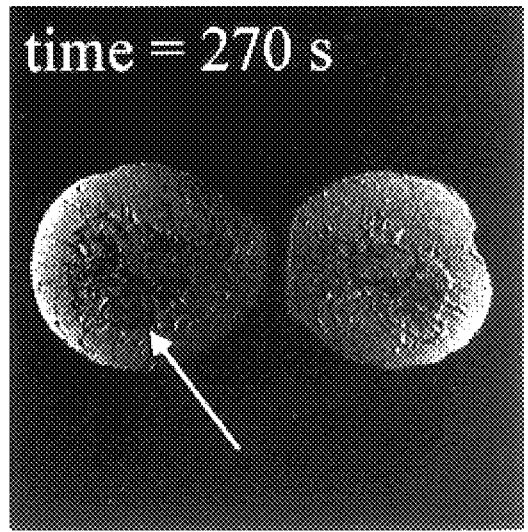
FIG. 1E is a flow chart of the method for merging of features of a lesion (or other abnormality) from an x-ray image (e.g., a mammogram), an ultrasound image (e.g., a sonogram), and/or an MR image for characterization of the lesion to determine a likelihood of malignancy, diagnosis, and/or prognosis, according to the present invention.

Accordingly, FIG. 1E is a flow chart of the method for merging of features of a lesion (or other abnormality) from an x-ray image (e.g., a mammogram), an ultrasound image (e.g., a sonogram), and/or an MR image for characterizing the lesion to determine a likelihood of malignancy, diagnosis, and/or prognosis. In FIG. 1E, in step 100 an image is acquired and in step 200 segmentation is performed to extract a suspect lesion. In step 300, features are extracted from the mammogram, MR, and ultrasound images which are classified at step 400 by a rule-based, analytic, and/or artificial neural network (ANN) classification technique. In step 500, the results visualization of the lesion is performed.

Figure 3:
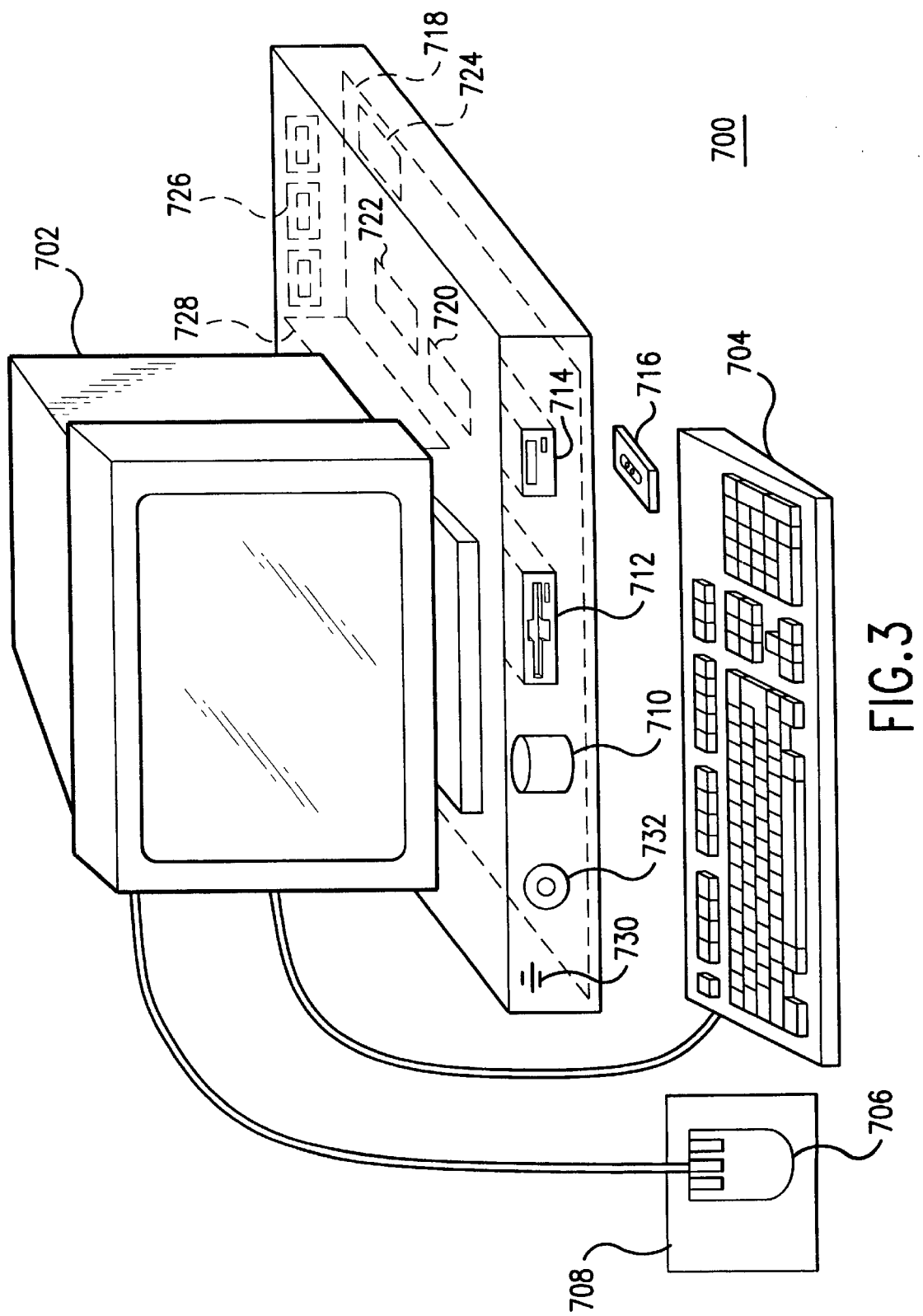
FIG. 3 is a detailed diagram of the computer of FIG. 2.

In FIG. 2, a system for implementing the processes of FIGS. 1A, 1C and 1E is shown including an image acquisition device 600, such as a computed radiography system, a laser scanner, MR imaging system, ultrasound imaging system, etc., and a computer 700, such as a general purpose computer. The computer 700 is shown in FIG. 3 and, for example, includes a display device 702, such as a touch screen monitor with a touch-screen interface, a keyboard 704, a pointing device 706, a digitizing pad 708, a hard disk 710, a floppy drive 712, a tape or CD ROM drive 714 with tape or CD media 716, a hard disk 710, floppy drive 712, a tape or CD ROM drive 714 with tape or CD media 716, and a mother board 718. The mother board 718 includes a processor 720, a RAM 722, and a ROM 724, 1/0 ports 726 which are used to couple to the image acquisition device 600, and optional specialized hardware 728 for performing specialized hardware/software fimctions, such as sound processing, image processing etc., a microphone 730, and a speaker or speakers 732.

Once an image is acquired by the image acquisition device 600, the computer 700, programmed with appropriate software, performs the processes of FIGS. 1A, 1C and 1E, such as the segmentation of the breast and lesions (step 200), the spatial, temporal, and/or hybrid feature extraction (step 300), the rule-based, analytic, and/or artificial neural network (ANN) classification (step 400), and the volume rendering, surface rendering, wire framing, and/or voxel modification visualization (step 500), the details of which will now be described with reference to the drawings.

Figure 4:
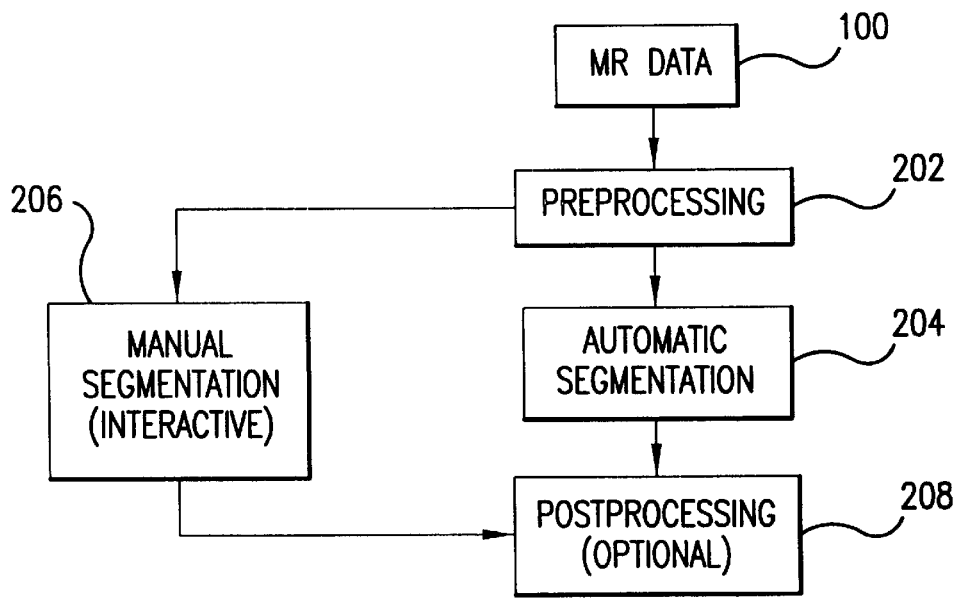
FIG. 4 is a flow chart of the method for segmentation of the breast in which to scan for malignancy, according to the present invention.

In the segmentation process (step 200, FIGS. 1A, 1C and 1E), a detection process consists of three steps: segmentation of the breast, localization of possible lesions, and segmentation of these possible lesions. The purpose of segmenting the breast region from the MR images is two-fold. First to obtain a volume of interest in which to scan for lesions. Second, to produce a rendering of the breast in order to visualize the location and shape of detected lesions with respect to the skin or the pectoralis muscle. In FIG. 4, after MR data is received at step 100 from the image acquisition device 600 (FIG. 2), the preprocessing step 202 performs spatial smoothing and/or temporal smoothing. At step 204, automatic segmentation of the breast is either achieved by global or local thresholding based on a histogram of voxel values, or by volume growing of the background starting from an initial point outside the breast region.

Figure 5:
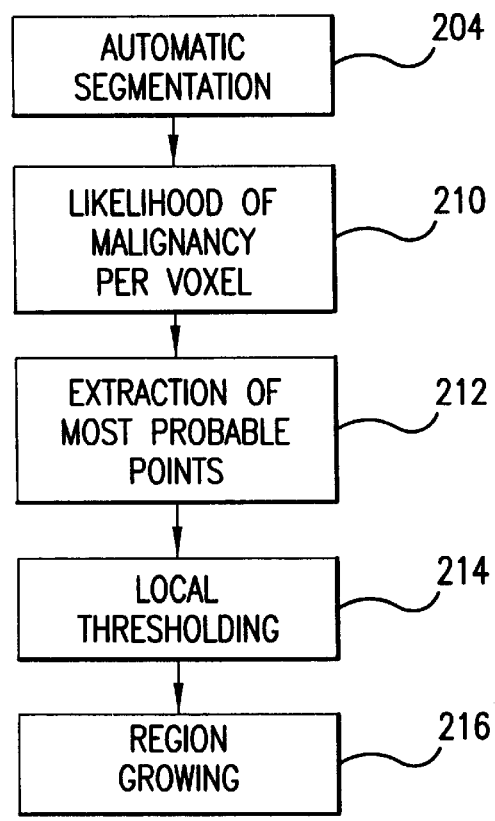
FIG. 5 is a flow chart illustrating the detection and segmentation of the lesion in order to obtain an initial estimate of the location of the lesion, followed by more accurate delineation of the margins, according to the present invention.

The aim of lesion localization is to obtain points in the breast corresponding to a high likelihood of malignancy. These points are presumably part of a lesion. Lesion segmentation aims to extract all voxels that correspond to the lesion. Lesion detection is either performed manually, using an interactive drawing tool, or automatically by isolating voxels that have a rate of contrast uptake higher than a pre-defined threshold value. Lesion segmentation is performed manually using an interactive drawing tool or automatically by image processing techniques based on local thresholding, region growing (2-D), and/or volume growing (3-D) (steps 204–216, FIG. 5).

After detection, the feature extraction stage is employed. This stage consists of three components (step 300, FIGS. 1A, 1C and 1E); extraction of temporal features, extraction of spatial features, and extraction of hybrid features. Features are mathematical properties of a set of voxel values that could reflect an underlying process of malignancy.

Figure 6A:
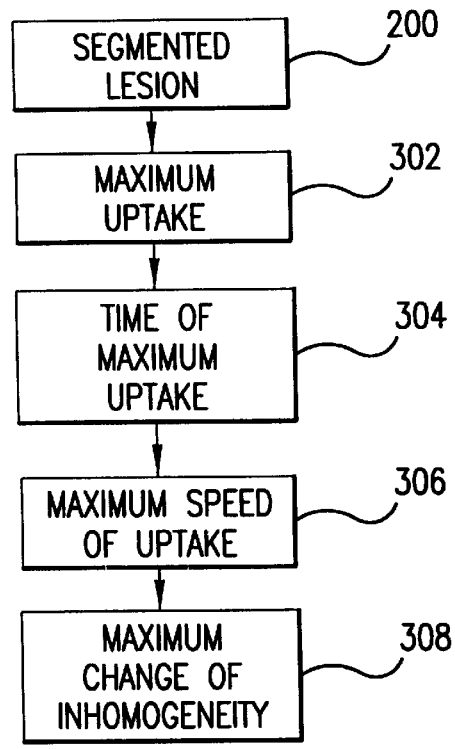
FIG. 6A is a flow chart illustrating the extraction of temporal features, wherein these features consider the uptake of contrast agent over time, according to the present invention.
Figure 6B:
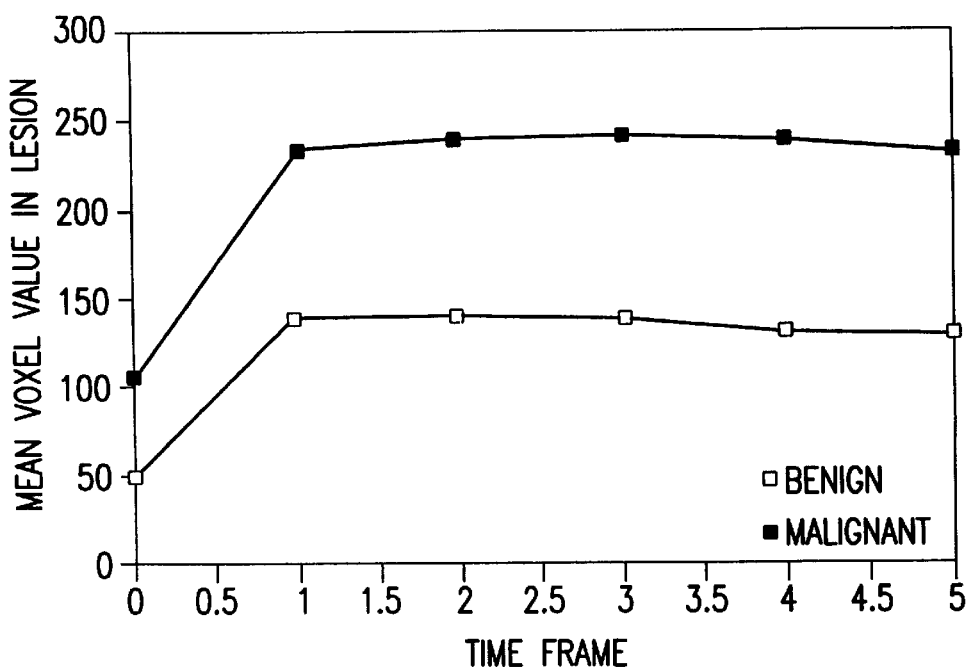
FIG. 6B is a graph illustrating the Gd-DTPA up-take curves for a benign lesion and a malignant lesion, wherein features can be extracted from such curves or from the image data directly, according to the present invention shows.

In FIG. 6A, temporal features are extracted by operators that quantify a trend of voxel values in time at fixed locations in space (steps 200–308). FIG. 6B shows up-take curves for a benign lesion and a malignant lesion. Features can be extracted from such curves or from the image data directly. Examples of such features are the maximum uptake of contrast agent within the lesion (step 302, FIG. 6A), the time frame at which that occurred (step 304, FIG. 6A), the maximum speed of uptake within the lesion (step 306, FIG. 6A), and the maximum change of inhomogeneity of uptake within the lesion (step 308, FIG. 6A). The speed of uptake is the maximum increase of the mean voxel value of the lesion and the inhomogeneity of uptake is the maximum increase in variance of the lesion voxel values. Most of these features need to be normalized to account for inter-patient differences in injected volume of contrast agent and differences in washout in other organs, such as the liver. Maximum uptake of contrast over time is computed (step 302, FIG. 6A) by taking the maximum of the ratio of the mean voxel value of the lesion at time frame n divided by the mean voxel value of the lesion at the first time frame, where n runs over all frame numbers as shown in the following equation:

$$\underset{n=1}{\overset{N}{\text{MAX}}}\left\{\frac{\text{mean lesion frame } n}{\text{mean lesion frame } 0}\right\} \quad (1)$$

The time of maximum uptake is calculated as shown in the following equation:

$$n \text{ at } \underset{n=1}{\overset{N}{\text{MAX}}}\left\{\frac{\text{mean lesion frame } n}{\text{mean lesion frame } 0}\right\} \quad (2)$$

The maximum speed of uptake is quantified by the maximum derivative of the flow curve. To perform normalization, the derivative is substituted by the maximum ratio of the mean voxel value at frame n+1 over the mean voxel value at frame n (step 306, FIG. 6A). The maximum speed of uptake is calculated as shown in the following equation:

$$\underset{n=0}{\overset{N-1}{\text{MAX}}}\left\{\frac{\text{mean lesion frame } n+1}{\text{mean lesion frame } n}\right\} \quad (3)$$

The maximum change in inhomogeneity of uptake is computed by the minimum of the ratio of the variance of the voxel values at frame n over the variance at frame n−i (step 306, FIG. 6A). The maximum change of inhomogeneity of uptake is calculated as shown in the following equation:

$$\underset{n=1}{\overset{N}{\text{MIN}}}\left\{\frac{\text{variance lesion frame } n}{\text{variance lesion frame } n-1}\right\} \quad (4)$$

Note that all temporal features for the purpose of classification are typically computed over the total volume of lesion voxels (3-D) (or over an area of lesion pixels (2-D)).

Figure 7A:
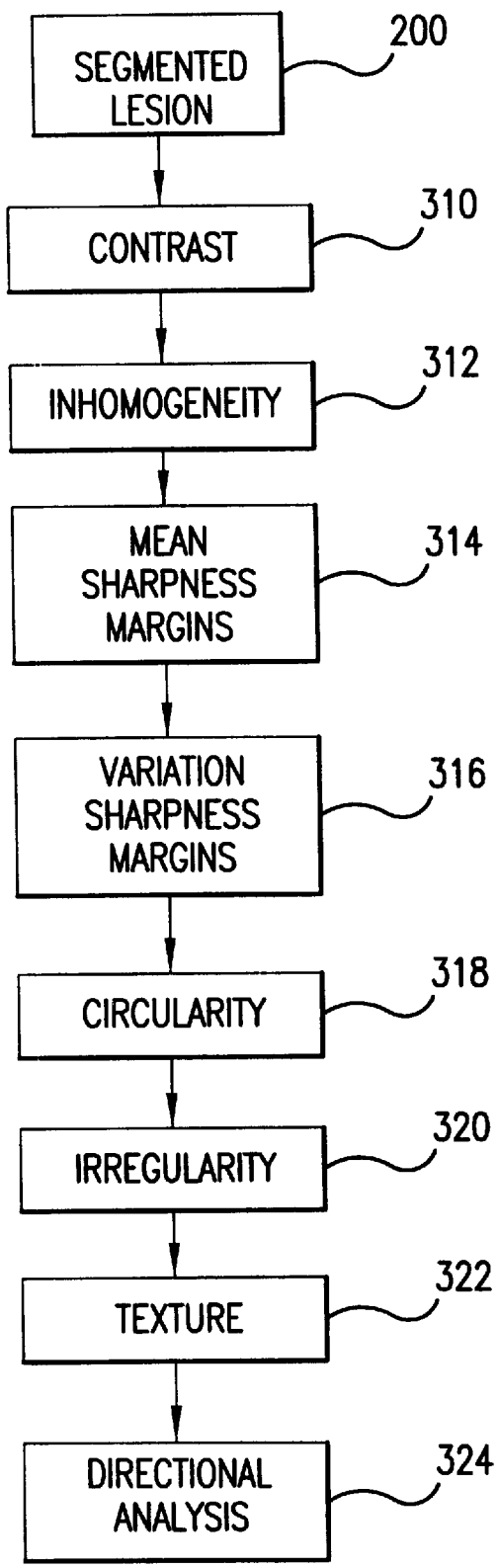
FIG. 7A is a flow chart illustrating the extraction of spatial features, wherein these features consider the spatial relation of neighboring voxel values, the geometry of the lesion margins, and/or the directionality of the gradients, according to the present invention.
Figure 7D:
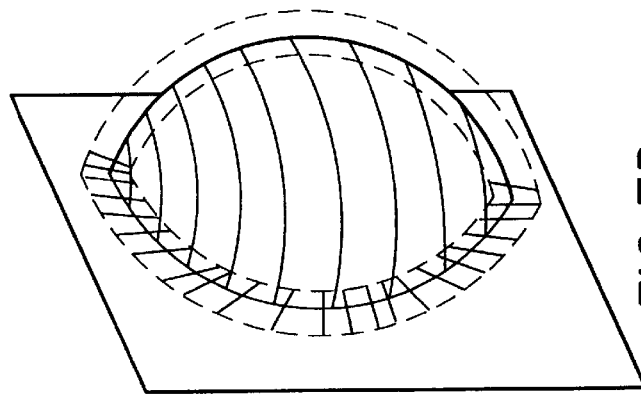
FIG. 7D is diagram for illustrating margin sharpness analysis of a lesion, according to the present invention.
Figure 7C:
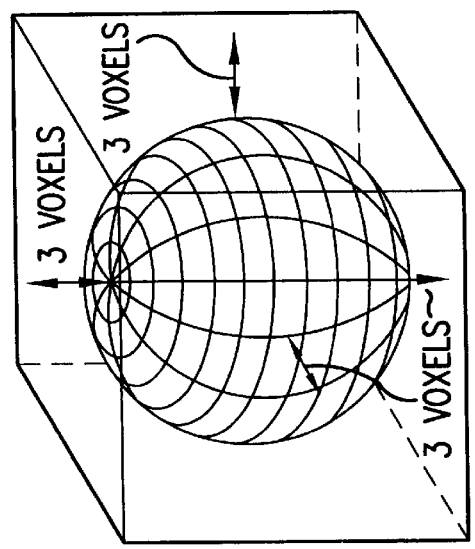
FIG. 7C is diagram for illustrating lesion contrast analysis of a lesion, according to the present invention.
Figure 7B:
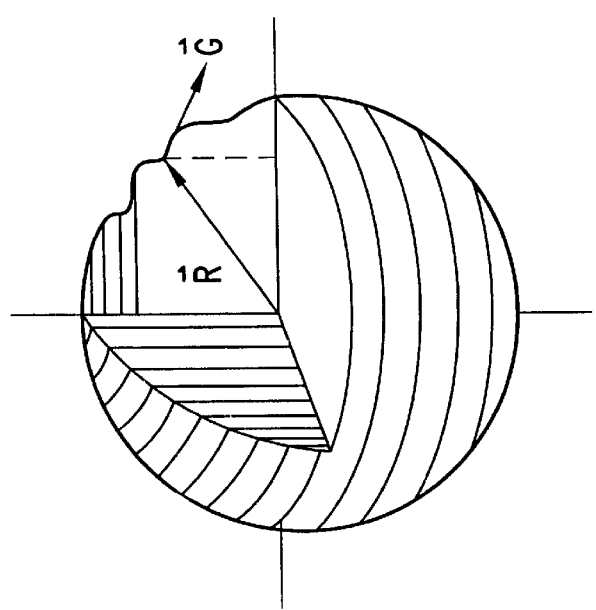
FIG. 7B is diagram for illustrating radial gradient analysis of a lesion, wherein R is a radial direction vector and G is a gradient direction vector, according to the present invention.

In FIG. 7A, spatial features are extracted by operators that quantify the spatial relation of voxel values with respect to neighboring values (steps 200–324). Examples of extracted features are the lesion contrast with respect to directly surrounding background (step 310), the inhomogeneity of voxel values in the lesion (step 312), mean sharpness and variation of sharpness along the lesion margins (steps 314 and 316), circularity and irregularity of the lesion (steps 318 and 320), texture (step 322), and directional analysis of gradients in, around, and/or about the lesion (step 324). The margin irregularity relates the volume of the lesion to the surface area of the lesion. The radial gradient analysis is a quantification of the extent to which the gradients inside the lesion are directed in a radial pattern form the center of the lesion (FIG. 7B). The margin gradient analysis is a quantification of the magnitude and variation of sharpness along the lesion margins.

To take full advantage of the 3-D nature of the data, the spatial features can be computed in 3-D, besides having equivalent features calculated in 2-D (steps 200–324, FIG. 7A). Lesion contrast is computed by the ratio of the mean voxel value of the lesion over the mean voxel value of the background in a surrounding rectangular box that has a margin of 3 voxels around the extremities of the lesion (FIG. 7C) as shown by the following equation:

$$\frac{\text{mean (lesion)}}{\text{mean (background)}} \quad (5)$$

The inhomogeneity of the voxel values in the lesion is quantified by the variance of the voxel values. Sharpness of the margin of the lesion is computed in two steps (FIG. 7D). First, a shell is extracted around the margin of the lesion by morphological dilation and erosion in 3-D. The shell has a thickness of 3 voxels (FIG. 7D). Next, a Sobel operator is applied with a 3-D kernel to quantify the magnitude of the gradients in the shell. The mean and variance of the gradient magnitudes is subsequently computed (steps 314 and 316).

Circularity and irregularity are computed (steps 318 and 320) by geometry-related equations that quantify how well the lesion conforms to a spherical shape, and how irregular the volume is distributed over space as shown by the following equations:

$$\frac{\text{effective volume}}{\text{volume}} \quad (6)$$

$$1 - \pi \cdot \frac{\text{effective diameter}^2}{\text{surface}} \quad (7)$$

where effective volume is the volume of the lesion in the lesion's present state (i.e., non-spherical), volume is the volume of a sphere having the same volume as the lesion, effective diameter is the diameter of the lesion, and surface is the surface area of the lesion. By comparing the effective volume of the lesion with the volume of the sphere how well the lesion conforms to a spherical shape is determined. Similarly, by comparing the effective diameter of the lesion with the surface area of the lesion how irregularly the volume of the lesion is distributed over space is determined.

Texture is quantified by computing the 2-D or 3-D Fourier transform of the voxel values within the lesion (step 322), referred to here as "power spectrum" as shown by the following equation:

$$\text{rms } \{F(\text{lesion})\} \quad (8)$$

The region or volume of interest is subjected to a texture analysis process that involves two measures: the root-mean-square (rms) variation (R) and the first moment of the filtered power spectrum (M), which represents the magnitude and coarseness of parenchymal texture pattern, respectively. Higher moments are not conceptualized visually as easily as the rms variation and first moment values, however, although they are also calculated.

Directional analysis of the gradients is computed in the lesion (step 324), and/or within the shell (FIG. 7D), and is aimed at quantifing how uniform the lesion extends along radial lines from a point in the center as shown by the following equations:

$$\sum_{i \in \text{lesion}} \frac{R_i \cdot G_i}{G_i} \quad (9)$$

$$\sum_{i \in \text{shell}} \frac{R_i \cdot G_i}{G_i} \quad (10)$$

This type of analysis shall be referred to here as "radial gradient analysis." In mammograms, it has been observed that the gradients in benign masses extend more uniform along radial lines than in malignant lesions. In 3-D, the radial gradient analysis is extended to spherical analysis. Two measures are extracted: the radial gradient index, and the radial gradient peak distinction. The radial gradient index is defined as the normalized mean dot product of the gradients in the lesion and the direction of the corresponding radials. The peak distinction is defined as the normalized standard deviation of the frequency of occurrence of these dot products.

Figure 8:
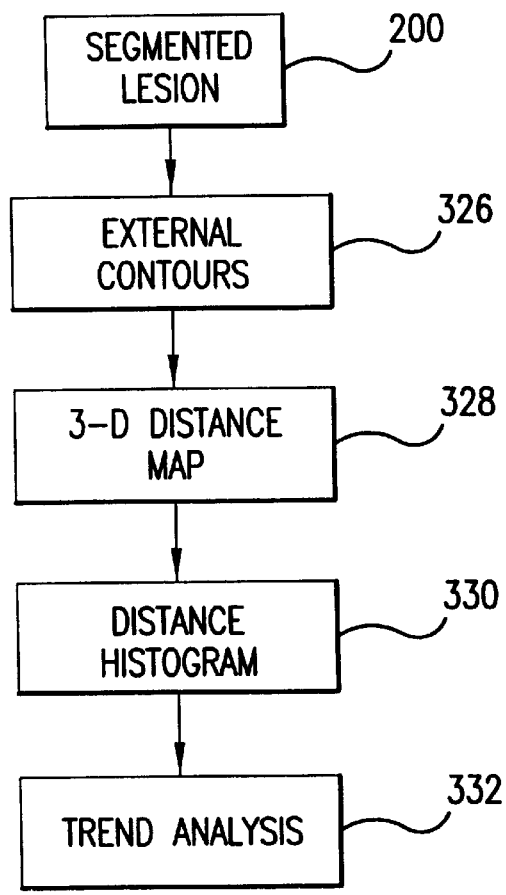
FIG. 8 is a flow chart illustrating the extraction of hybrid features, wherein these feature consider properties of a lesion in both temporal as well as spatial domain, according to the present invention.

In FIG. 8, hybrid features are used to consider voxel values in both time as well as space (steps 200–332). An example is flow analysis. Flow analysis is aimed at quantifying the direction of the flow of contrast agent in the lesion. Due to a mechanism of tumor growth, it has been observed that some malignant lesions can be characterized by a flow of contrast agent from the margins inwards, and some benign lesions by a flow outwards towards the margins. In addition, it has been observed that the amount of uptake may be larger at the margin of some lesions (such as some malignant lesions) than at the center, whereas the amount of uptake may be less at the margin for other lesions (such as some benign lesions).

Figure 19:
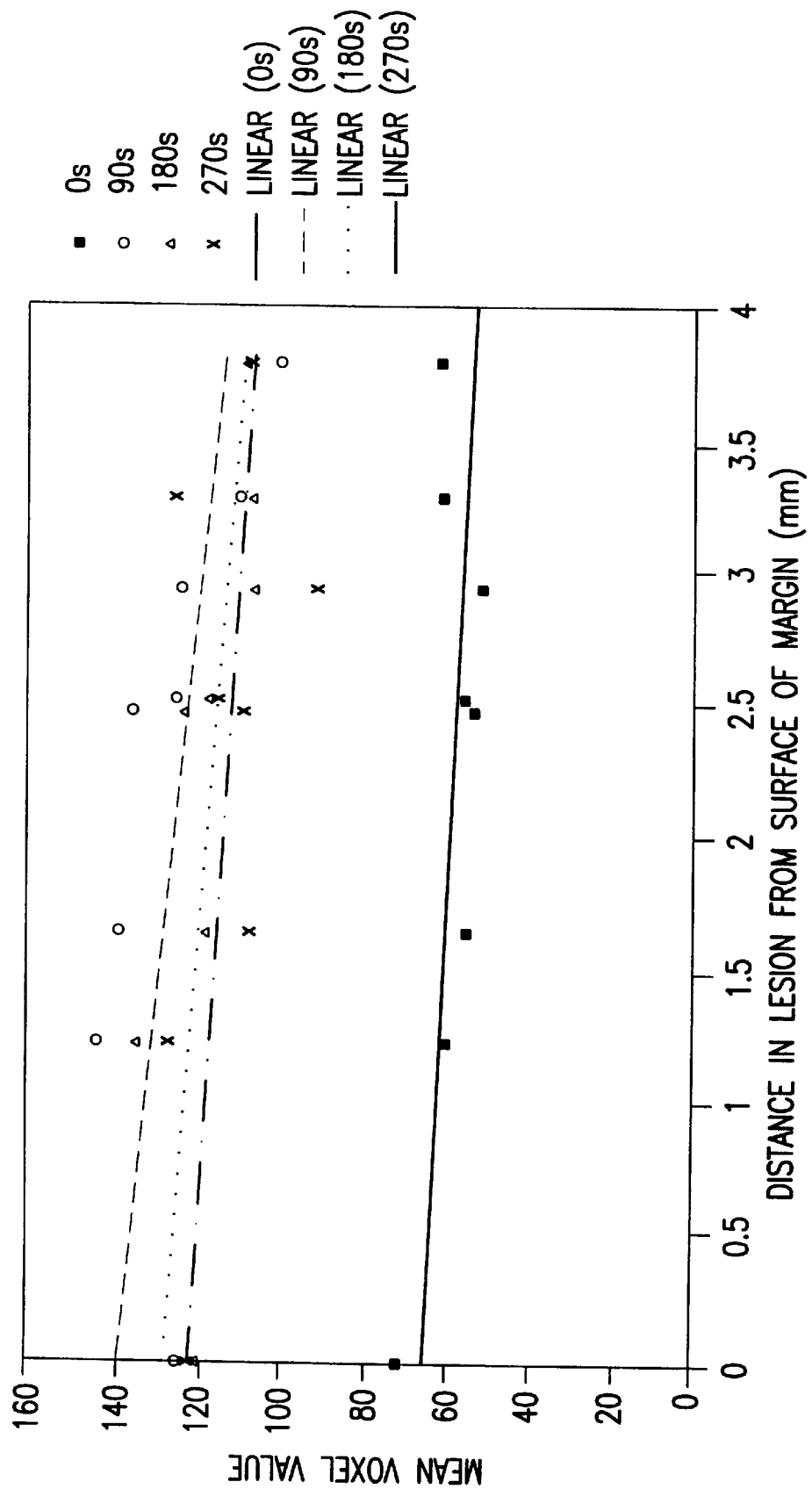
FIG. 19 is a graph illustrating the performance of the hybrid features in characterizing a malignant lesion, wherein the flow analysis shows the mean voxel value as a function of the distance in the lesion from the surface of the lesion, and the Gd-DTPA uptake is larger at the margins in three dimension, according to the present invention.

Flow analysis consists of three stages. In the first stage, the outer surface of the lesion margin is identified (step 326). Next, in step 328, a distance transform is applied in 3-D to the surface (or similarly in 2-D from the margin). The distance transform yields a map of the volume in which each voxel receives a value proportional to its distance to the nearest surface point. Distances outside the lesion are negated, so that only distances inside the lesion are included in further calculations. Next a histogram is computed that bins the frequency of occurrence of voxel values at fixed distances (shells) from the surface (step 330). In the third stage a line is fitted to this histogram of distances to analyze the trend (step 332). If the uptake of contrast is larger at the center, the line will have a positive slope (FIG. 20) and if the uptake of contrast is larger at the margin of the lesion the line will have a negative slope will be negative (FIG. 19). In addition, if the line has a positive slope throughout time, the flow of contrast is outwards. If the slope is negative, the flow is inwards. It is likely that the efficacy of this feature as well other temporal features is limited by the time interval between subsequent MR scans in the dynamic series. Similarly, the efficiency of the spatial features is limited by the spatial resolution of the MR scans. Subsequently, a satisfactory trade-off between temporal and spatial resolution needs to be made.

Figure 9:
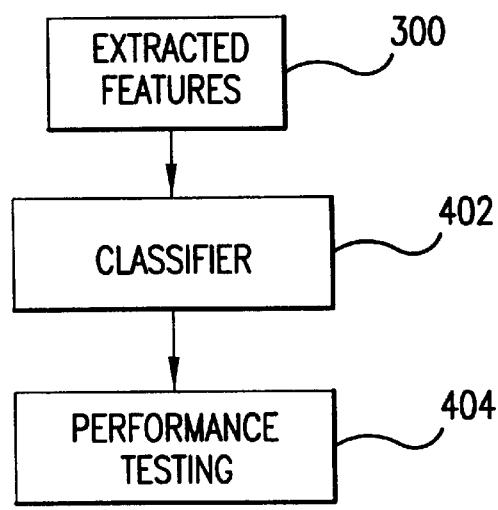
FIG. 9 is a flow chart illustrating the merging of different features into a diagnosis of an estimate of malignancy using different classification schemes, according to the present invention.

In FIG. 9, after the feature extraction stage, the various features are merged into an estimate of malignancy in the classification stage (steps 200–404). Artificial neural networks, analytic classifiers as well as rule-based methods can be applied for this purpose (step 402). The output from the neural network or other classifier can be used in making a diagnosis and/or prognosis. For example, with the analysis of the MR images of the breast the features can be used to either distinguish between malignant and benign lesions, or distinguish between the types of benign lesions such as fibroadenoma, papilloma, or benign mastopathy. The step of classification (step 402) is then typically followed by performance testing (step 404) to evaluate the system's performance.

Figure 10:
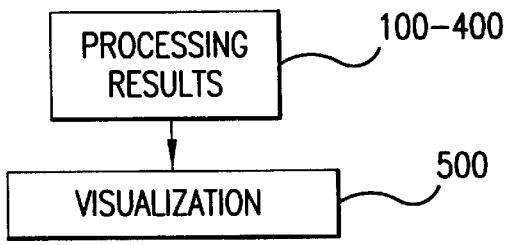
FIG. 10 is a flow chart illustrating visualization of a lesion with respect to surrounding tissue in order to visually examine the mass with respect to a known reference, according to the present invention.

In FIG. 10, assessing lesion malignancy can also be accomplished with visualization (steps 100–500). The purpose of visualization is to show the shape, size, and location of the tumor with respect to known reference tissue (step 500). Several methods can be used for this purpose such as surface rendering, volume rendering and wire framing with cut planes. In addition, once the lesion and the tissues in the breast are identified, an anatomical relevant look-up table can be used to enhance the characteristics of the lesion as will be described later with reference to steps 100–500 of FIG. 11.

The MR data can be segmented in such way that it becomes suitable for visual and/or computerized comparison with images obtained from other modalities such as X-ray (mammography) and ultra-sound (echo). An advantage of such comparison is to improve the performance of the diagnosis of breast cancer beyond the point reached from analysis of each individual modality alone. In addition, diagnosis by a physician may be facilitated when the MR data is rendered similar visual appearance as mammograms. For computerized analysis, rendering similar appearance is also desired to allow automated image comparison techniques, such as registration by maximization of cross correlation, to be possible. For the purposes of the present invention, the breast can be considered to exist of three different types of tissue only: fat, parenchyma, and tumor. Different imaging modalities generally map these tissues to different gray value regions. In addition, the MR data is of a 3-D nature, while mammograms are strictly 2-D. In the present invention the gray values are transformed so that they map to similar gray value regions and project the 3-D image to the plane of the mammogram.

Figure 11:
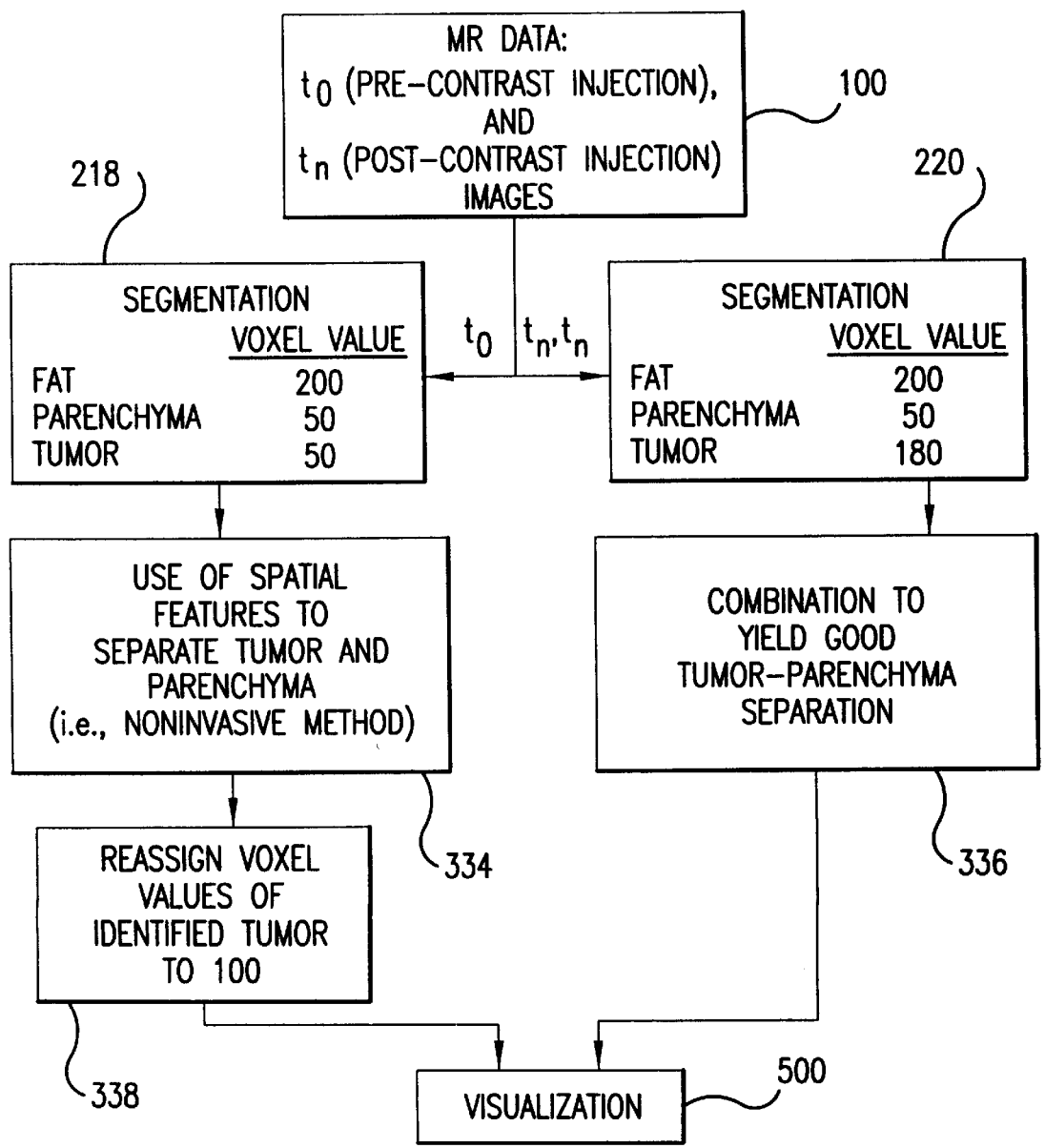
FIG. 11 is a flow chart illustrating the method for visualization of a lesion with enhancement after application of an anatomically relevant look-up table that modifies the voxel value of the lesion, according to the present invention.

In FIG. 11, the novel display technique consists of four stages. First, the extent of the tumor is found by similarity mapping (step 218). Second, tumor and parenchyma are extracted by multi-modal analysis of the histogram of pixel values (steps 334 and 336). Third, the gray values of the individual regions are mapped to the corresponding range of these regions in mammograms (step 338). Finally, the 3-D MR data is projected to obtain a mammogram-like image (step 500).

Similarity mapping consists of several stages. First, a region of interest is selected manually or automatically inside the lesion. The mean contrast uptake curve is examined in this region (FIG. 6B), and this curve is correlated with all other voxels in the breast in order to determine the location and extent of regions that exhibit the same uptake properties. Separation of remaining breast tissue in fat and dense can, for example, be performed by multi-modal segmentation (steps 218 and 220, FIG. 11). Assuming two classes of image pixels (i.e., gray value regions with similar properties), two threshold values are derived, that maximize the interclass variance between the different regions. Once the different regions in the breast have been identified, their pixel values are mapped to a normalized range by a combination of contrast stretching, windowing and level scaling (step 338, FIG. 11).

FIGS. 12–23 illustrate the performance of some of the individual and combined features in a preliminary study. In this study, dynamic MR data was obtained from 27 patients by a T1-weighted sequence, using 64 coronal slices, a typical slice thickness of 2 mm, and a pixel size of 1.25 mm. After injection of Gd-DTPA contrast, 4 to 6 scans of both breasts were obtained at 90 second time intervals. The database contained 13 benign and 15 malignant lesions. The computerized classification method of the present invention included temporal as well as spatial features. Preliminary results indicate that the most efficient combination is radial gradient peak distinction and margin irregularity, resulting in an Az value of 0.95. At a sensitivity of 100%, the maximum fraction of unnecessary biopsies avoided is estimated to be 40%.

Figure 12:
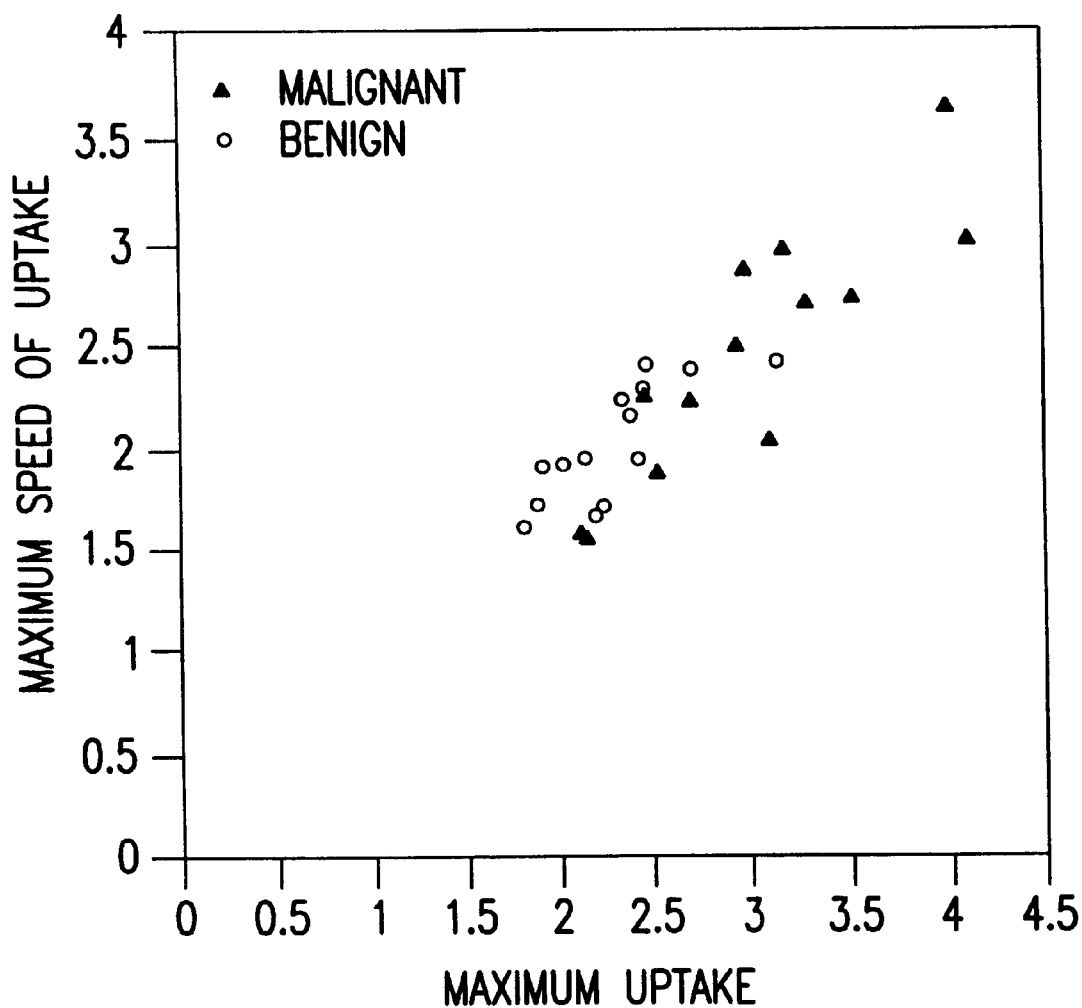
FIG. 12 is a graph illustrating the performance of the temporal features of uptake and speed of uptake of Gd-DTPA in the lesion (calculated in terms of volume) in distinguishing between malignant and benign lesions, according to the present invention.

FIG. 12 is a graph illustrating the performance of the temporal features of uptake and speed of uptake of Gd-DTPA in the lesion (calculated in terms of volume) in distinguishing between malignant and benign lesions, according to the present invention.

Figure 13:
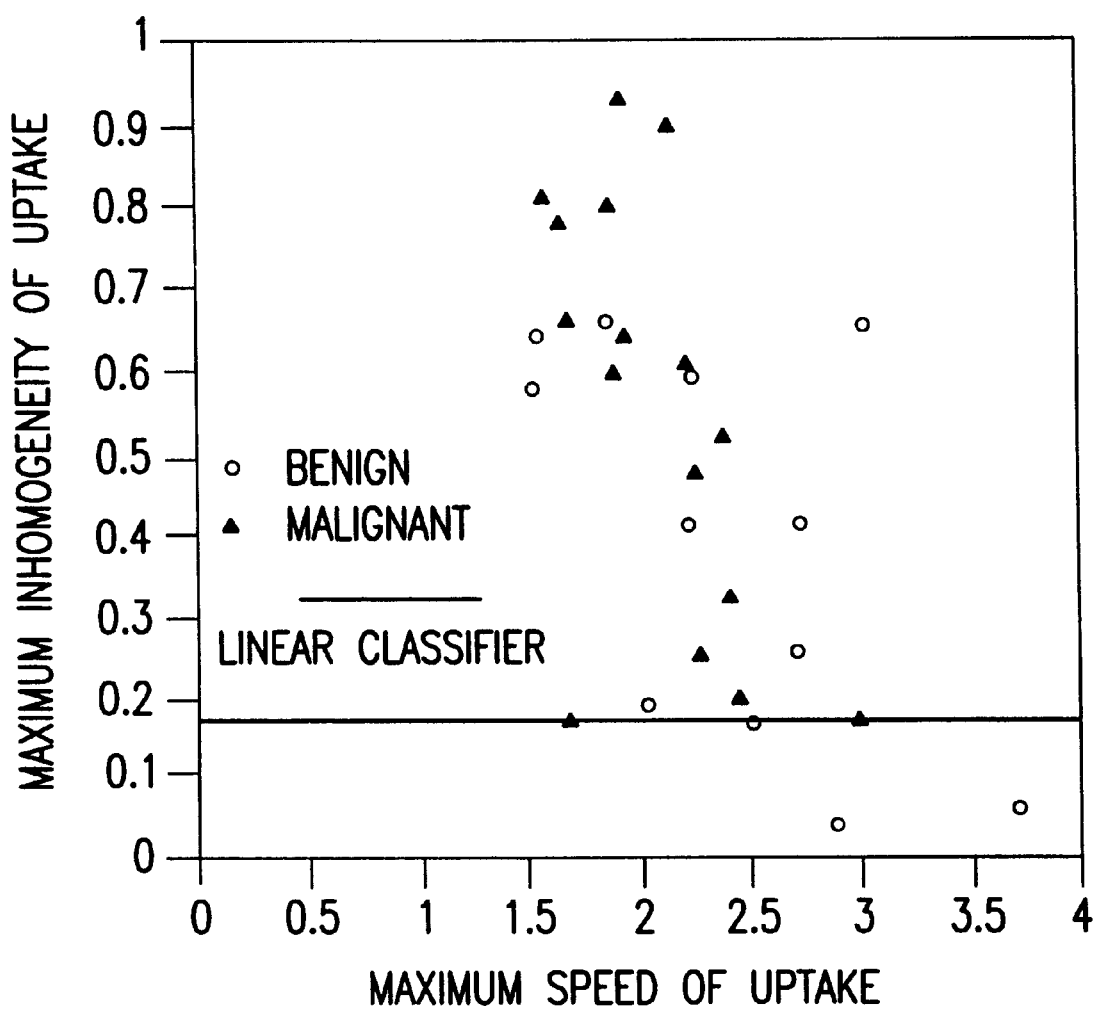
FIG. 13 is a graph illustrating the performance of the temporal features of speed and inhomogeneity of Gd-DTPA uptake in the lesion (calculated in terms of volume) in distinguishing between malignant and benign lesions, according to the present invention.

FIG. 13 is a graph illustrating the performance of the temporal features of speed and inhomogeneity of Gd-DTPA uptake in the lesion (calculated in terms of volume) in distinguishing between malignant and benign lesions, according to the present invention.

Figure 14:
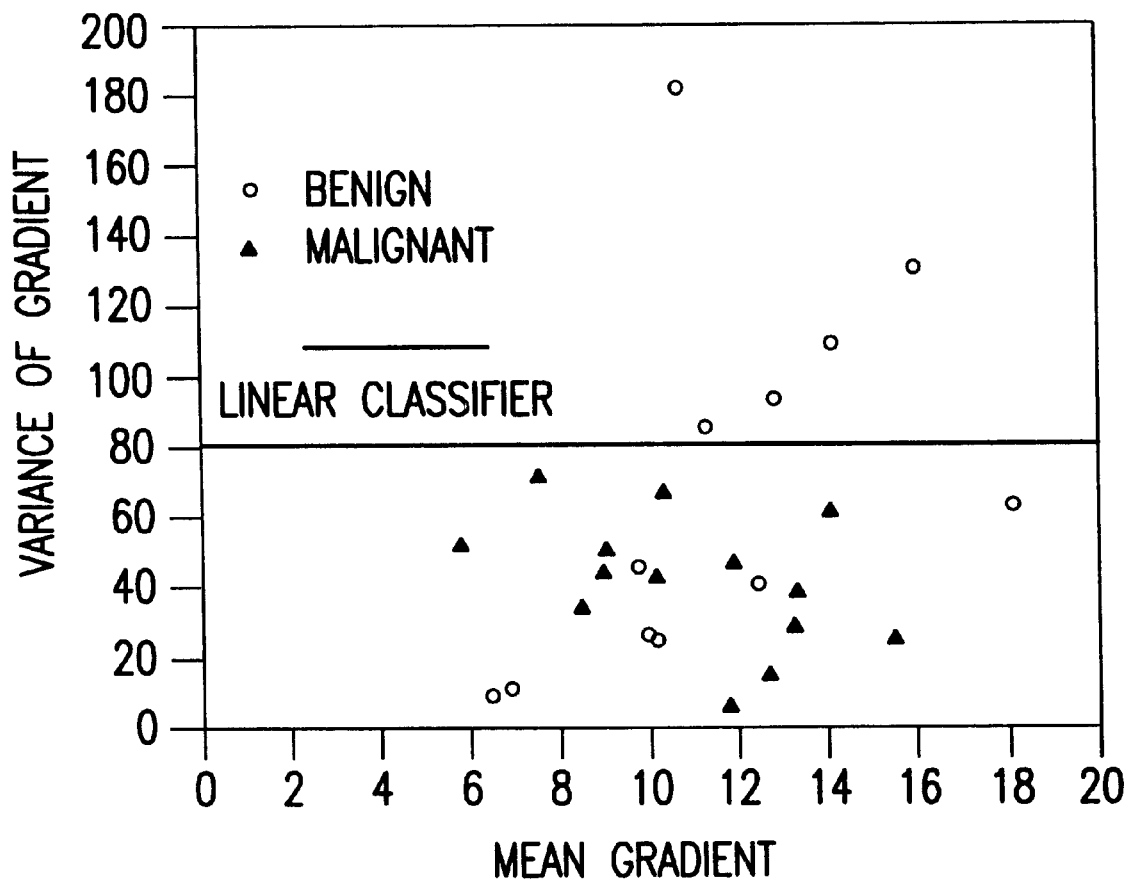
FIG. 14 is a graph illustrating the performance of the spatial features related to an analysis of sharpness of lesion margins (calculated in three dimensions) in distinguishing between malignant and benign lesions, wherein the spatial features are the mean and variance of the gradient along the margin of the lesion, according to the present invention.

FIG. 14 is a graph illustrating the performance of the spatial features related to an analysis of sharpness of lesion margins (calculated in three dimensions) in distinguishing between malignant and benign lesions, wherein the spatial features are the mean and variance of the gradient along the margin of the lesion, according to the present invention.

Figure 15:
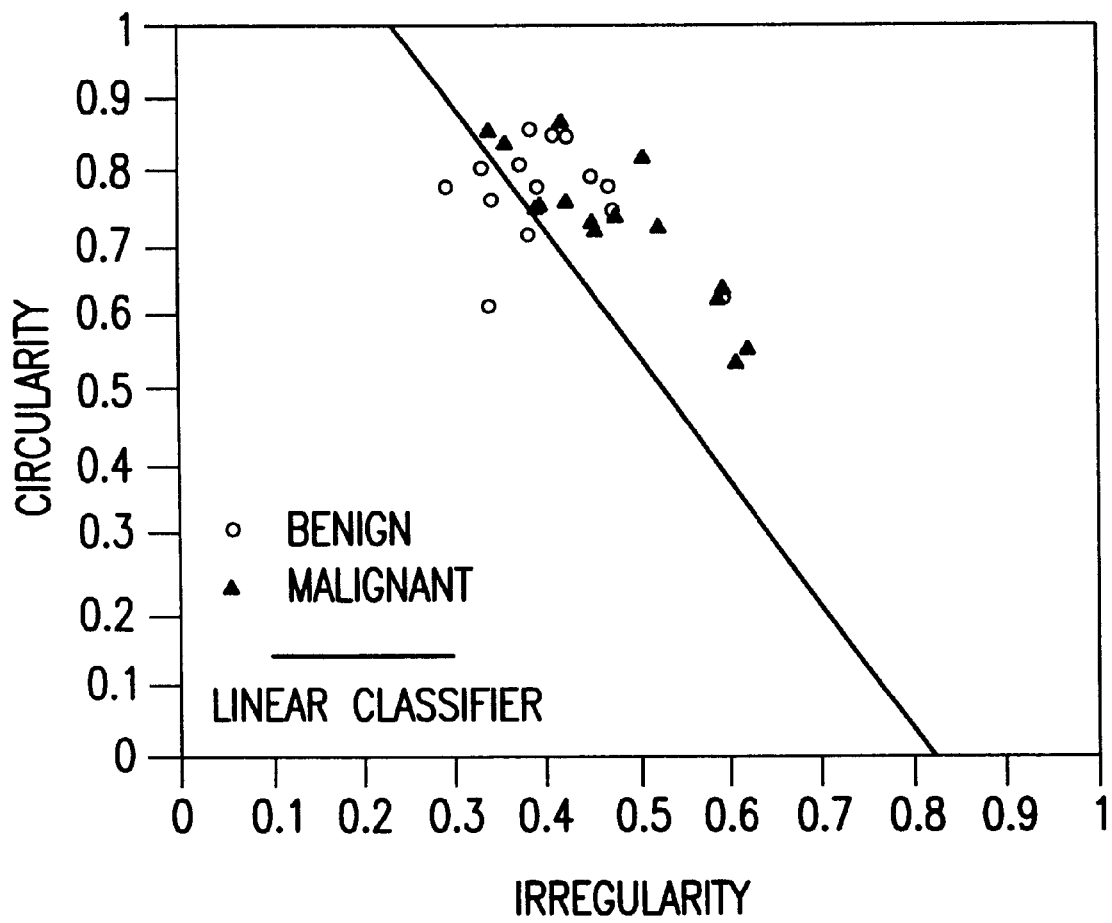
FIG. 15 is a graph illustrating the performance of the spatial features related to an analysis of lesion margins (calculated in three dimensions) in distinguishing between malignant and benign lesions, wherein the spatial features are the irregularity and circularity of the lesion, according to the present invention.

FIG. 15 is a graph illustrating the performance of the spatial features related to an analysis of lesion margins (calculated in three dimensions) in distinguishing between malignant and benign lesions, wherein the spatial features are the irregularity and circularity of the lesion, according to the present invention.

Figure 16:
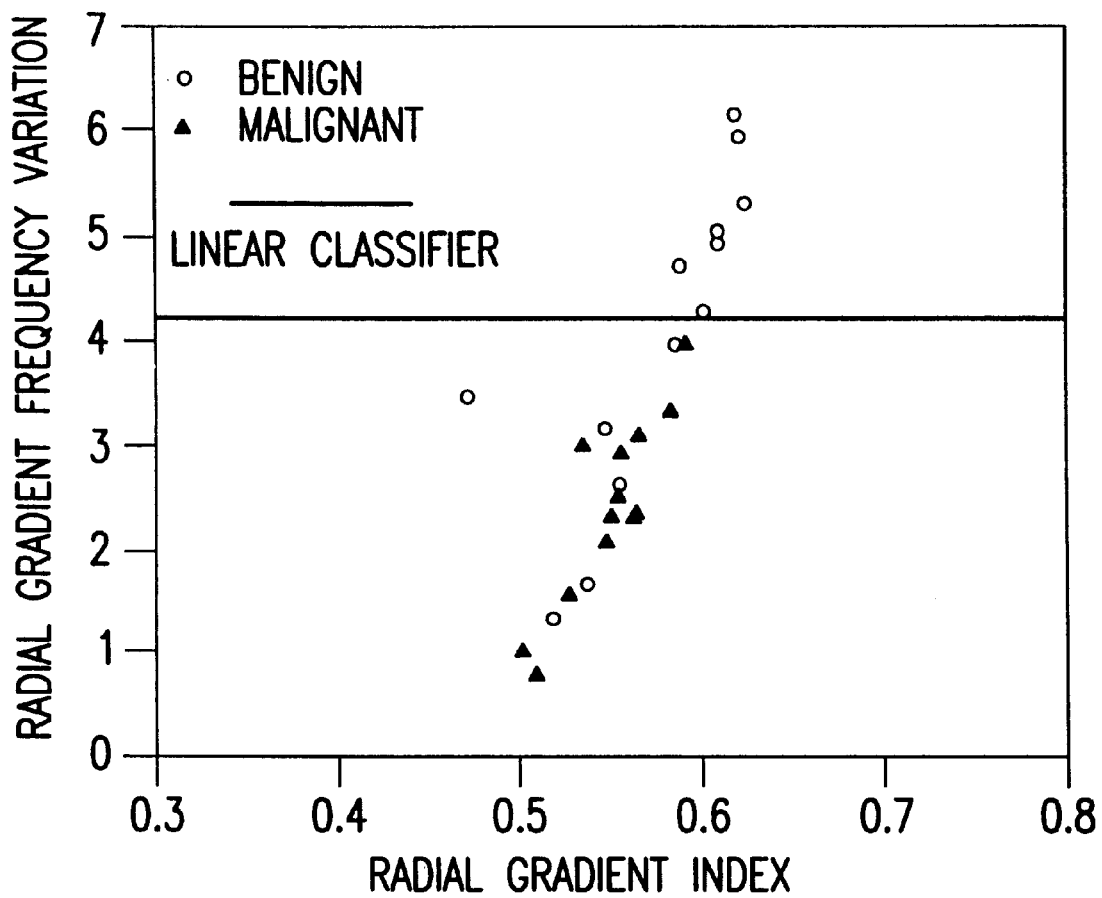
FIG. 16 is a graph illustrating the performance of the spatial features related to a radial analysis of lesions (calculated in three dimensions) in distinguishing between malignant and benign lesions, wherein the spatial features are the radial gradient index and the radial gradient frequency variation of the lesion, according to the present invention.

FIG. 16 is a graph illustrating the performance of the spatial features related to a radial analysis of lesions (calculated in three dimensions) in distinguishing between malignant and benign lesions, wherein the spatial features are the radial gradient index and the radial gradient frequency variation of the lesion, according to the present invention.

Figure 17:
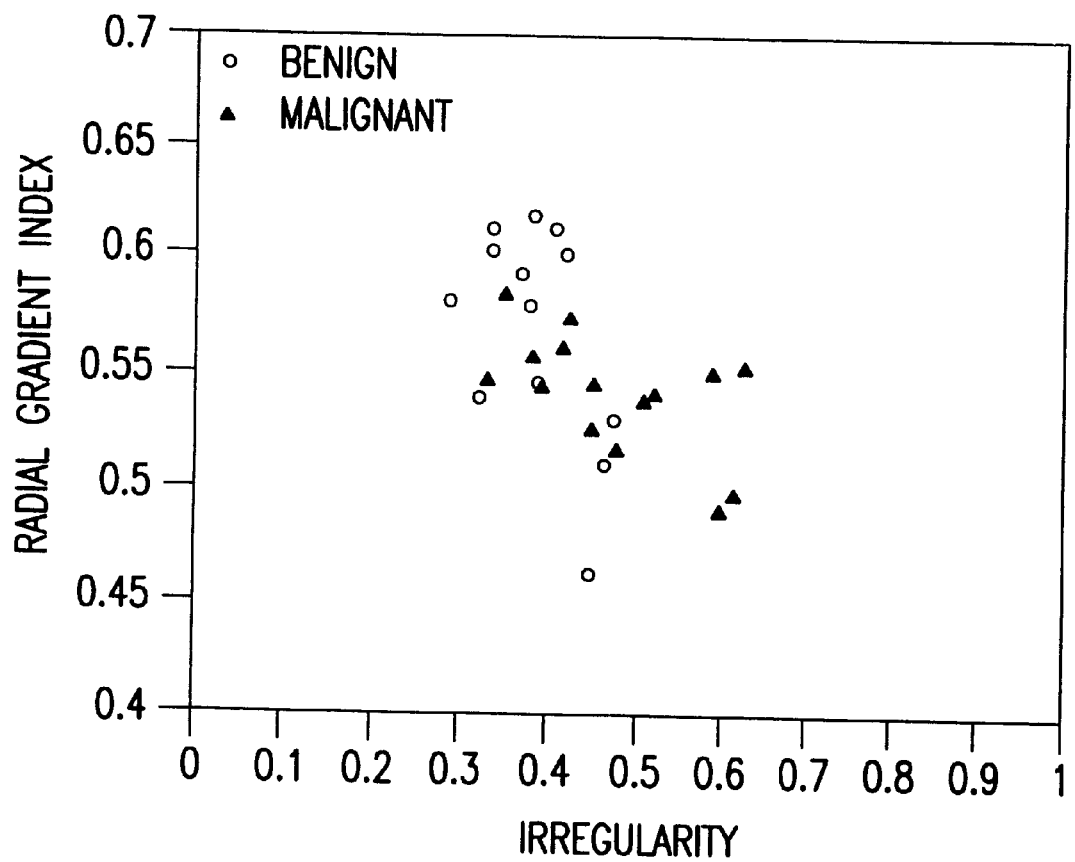
FIG. 17 is a graph illustrating the performance of the spatial features related to an analysis of geometric shape and sharpness of lesion margins (calculated in three dimensions) in distinguishing between malignant and benign lesions, wherein the spatial features are the irregularity and radial gradient index of the lesion, according to the present invention.

FIG. 17 is a graph illustrating the performance of the spatial features related to an analysis of geometric shape and sharpness of lesion margins (calculated in three dimensions) in distinguishing between malignant and benign lesions, wherein the spatial features are the irregularity and radial gradient index of the lesion, according to the present invention.

Figure 18:
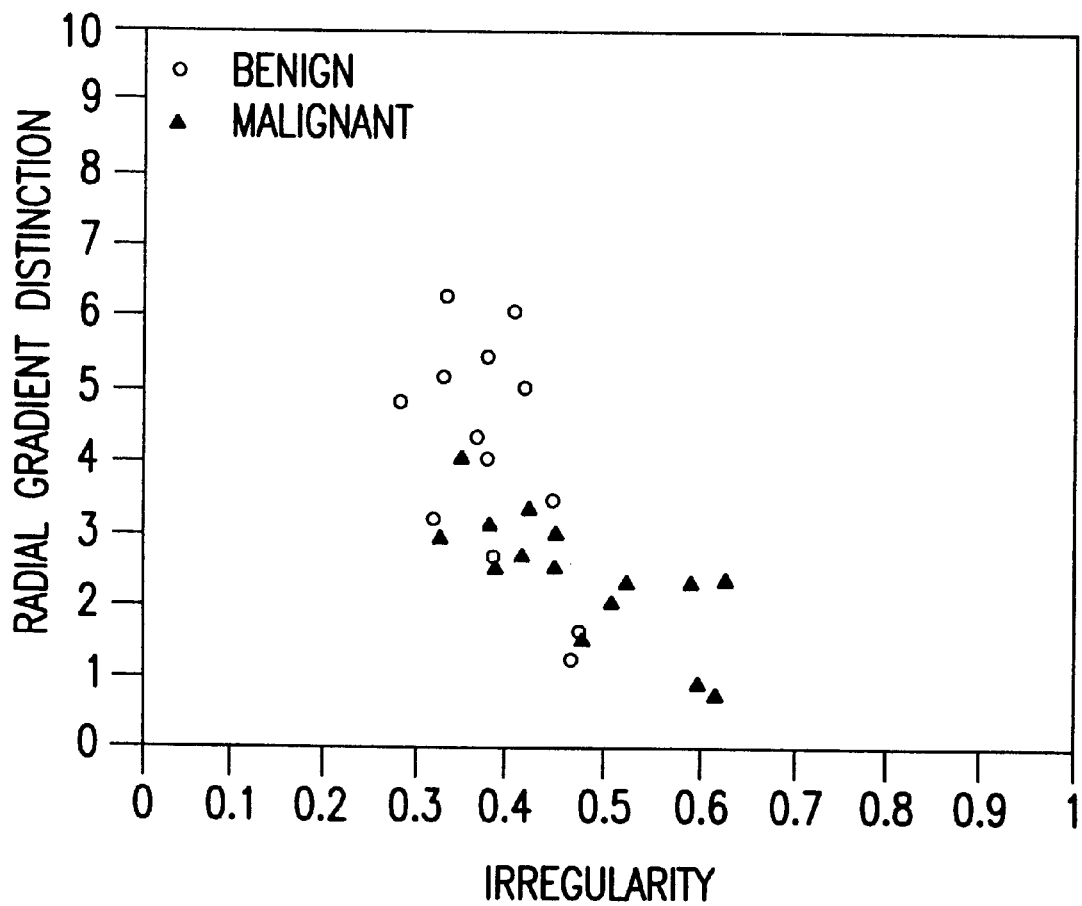
FIG. 18 is a graph illustrating the performance of the spatial features related to an analysis of geometric shape and sharpness of lesion margins (calculated in three dimensions) in distinguishing between malignant and benign lesions, wherein the spatial features are the irregularity and radial gradient distinction of the lesion, according to the present invention.

FIG. 18 is a graph illustrating the performance of the spatial features related to an analysis of geometric shape and sharpness of lesion margins (calculated in three dimensions) in distinguishing between malignant and benign lesions, wherein the spatial features are the irregularity and radial gradient distinction of the lesion, according to the present invention.

FIG. 19 is a graph illustrating the performance of the hybrid features in characterizing a malignant lesion, wherein the flow analysis shows the mean voxel value as a finction of the distance in the lesion from the surface of the lesion, and the Gd-DTPA uptake is larger at the margins in three dimension, according to the present invention.

Figure 20:
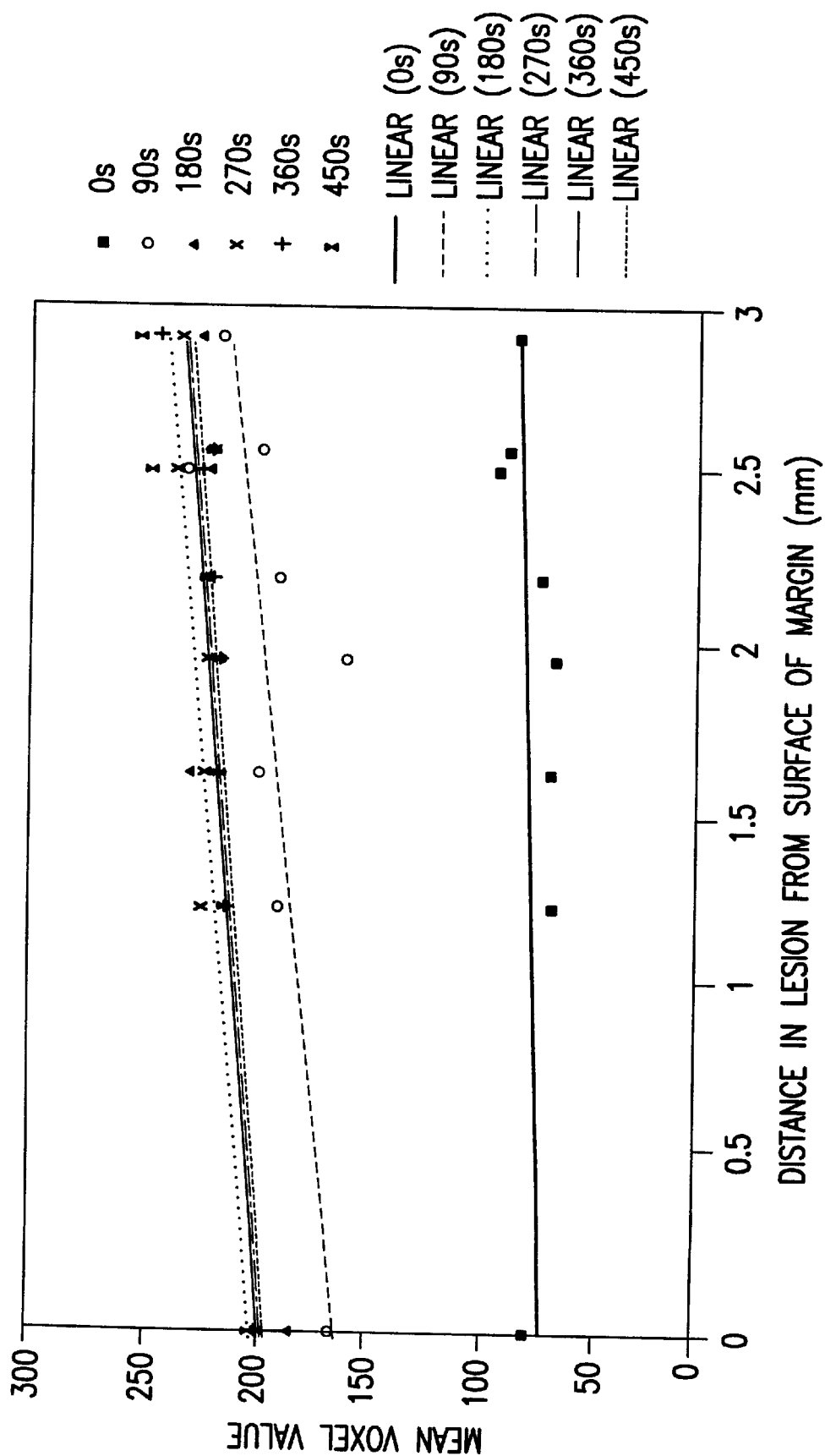
FIG. 20 is a graph illustrating the performance of the hybrid features in characterizing a benign lesion, wherein the flow analysis shows the mean voxel value as a function of the distance in the lesion from the surface of the lesion, and the Gd-DTPA uptake is smaller at the margins in three dimension, according to the present invention.

FIG. 20 is a graph illustrating the performance of the hybrid features in characterizing a benign lesion, wherein the flow analysis shows the mean voxel value as a finction of the distance in the lesion from the surface of the lesion, and the Gd-DTPA uptake is smaller at the margins in three dimension, according to the present invention.

Figure 21:
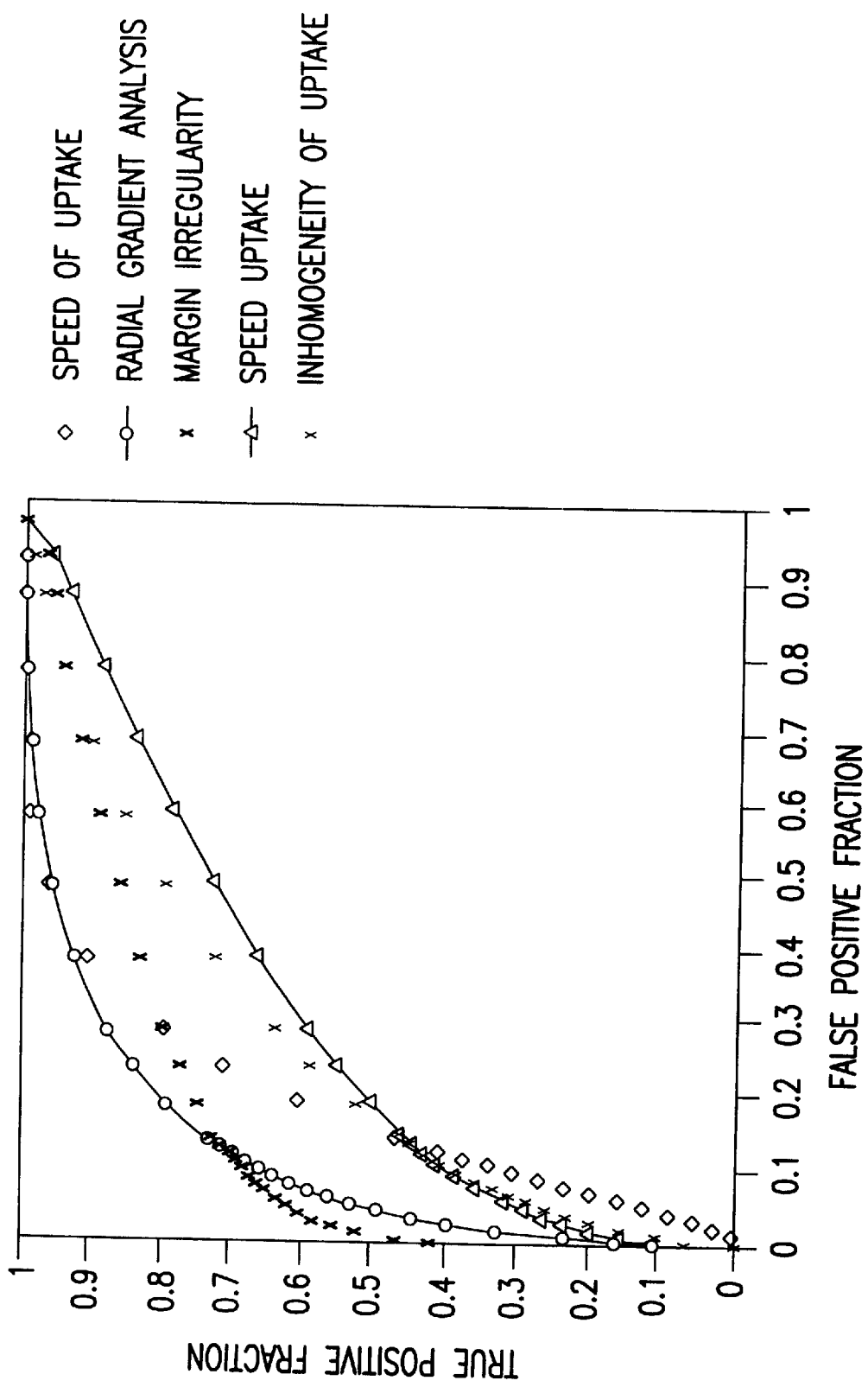
FIG. 21 is a graph illustrating the performance of individual features in the task of distinguishing between malignant and benign lesion on MR images of the breast, according to the present invention.

FIG. 21 is a graph illustrating the performance of individual features in the task of distinguishing between malignant and benign lesion on MR images of the breast, according to the present invention.

Figure 22:
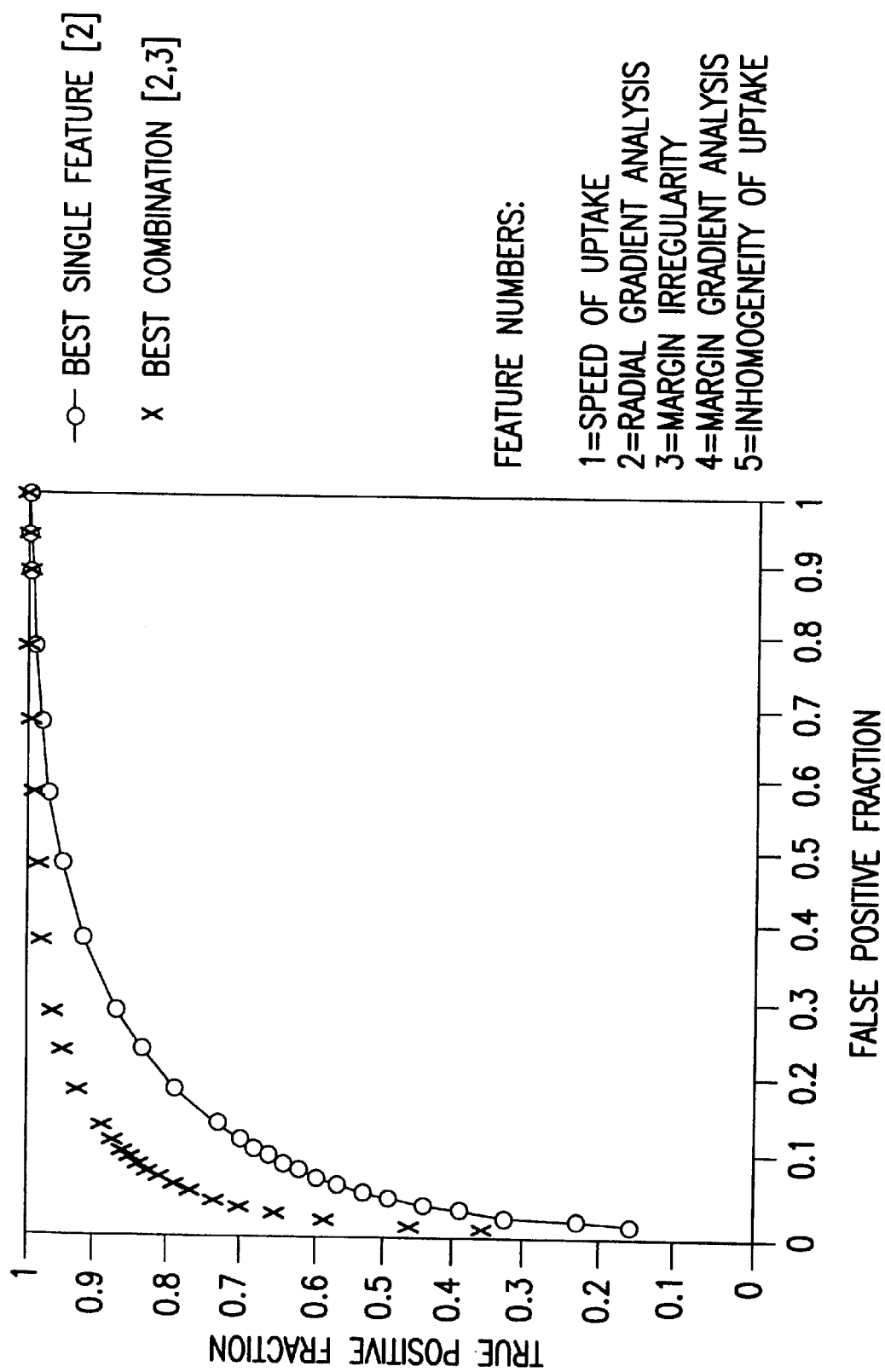
FIG. 22 is a graph illustrating the performance of one of the best individual features and a combination of features in the task of distinguishing between malignant and benign lesion on MR images of the breast, according to the present invention.

FIG. 22 is a graph illustrating the performance of one of the best individual features and a combination of features in the task of distinguishing between malignant and benign lesion on MR images of the breast, according to the present invention.

Figure 23A:
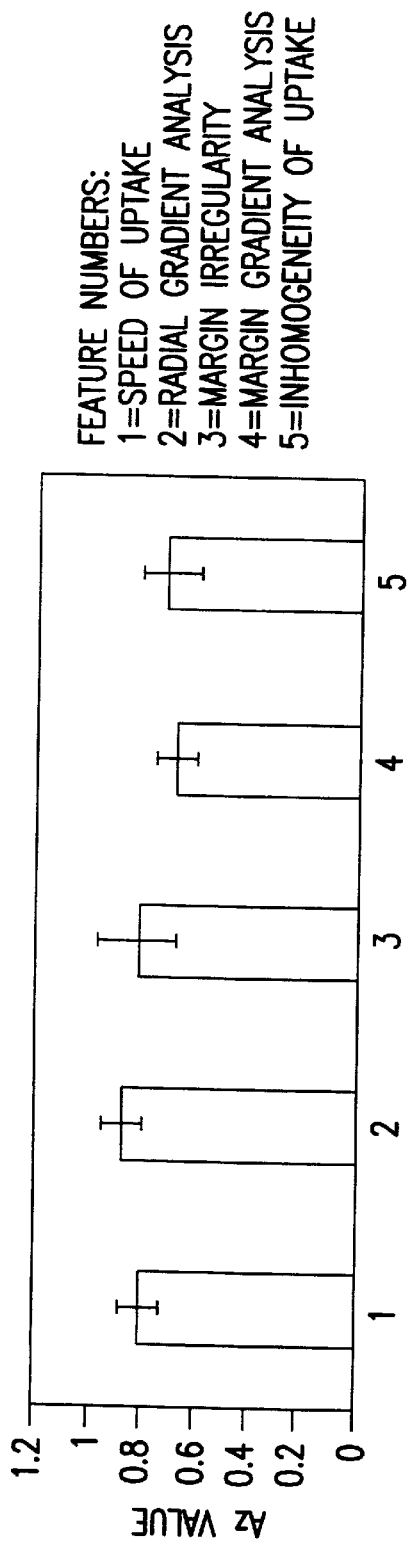
FIG. 23 is a graph illustrating the performance (in terms of area under the ROC curve(Az)) of individual features and combination of features in the task of distinguishing between malignant and benign lesion on MR images of the breast, according to the present invention.
Figure 23B:
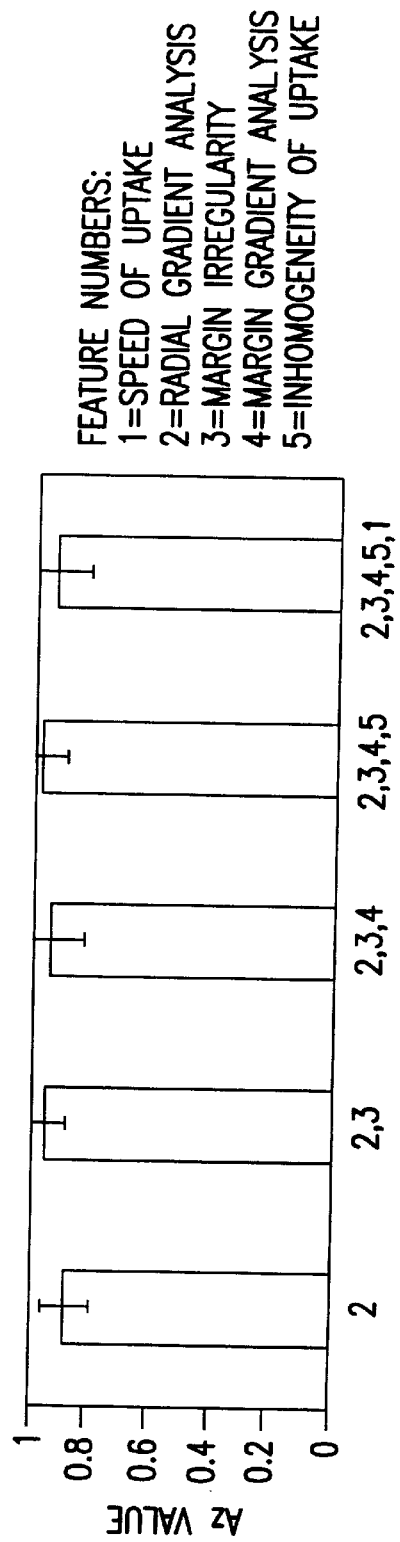

FIG. 23 is a graph illustrating the performance (in terms of area under the ROC curve(Az)) of individual features and combination of features in the task of distinguishing between malignant and benign lesion on MR images of the breast, according to the present invention.

Although in the preferred embodiment, the system is described in terms automated method and system for the characterization of lesions using computer-extracted features from MR images of the breast, the processes of the present invention can be applied to characterization of other types of abnormal anatomic regions in projection medical images, such as chest radiographs, and/or in volume medical, such as tomographic scans, as will be readily apparent to those skilled in the art.

The present invention includes a computer program product, for implementing the processes of the present invention (as above described), which may be on a storage medium including instructions and/or data structures which can be used to program the computer 700 (FIGS. 2 and 3) to perform processes of the invention. The storage medium can include, but is not limited to, any type of disk including floppy disks, optical discs, CD-ROMs, and magneto-optical disks, ROMs, RAMs, EPROMs, EEPROMs, magnetic or optical cards, or any type of media suitable for storing electronic instructions (e.g., the hard disk 710, the floppy drive 712, the tape or CD ROM drive 714 with the tape or the CD media 716, the RAM 722, and the ROM 724). However, this invention may be implemented by the preparation of application specific integrated circuits or by interconnecting an appropriate network of conventional component circuits, as will be readily apparent to those skilled in the art.

Obviously, numerous modifications and variations of the present invention are possible in light of the above teachings. It is therefore to be understood that within the scope of the appended claims, the invention may be practiced otherwise than as specifically described herein.

What is claimed as new and desired to be scured by Letters Patent of the United States is:

1. A method for the analysis of a lesion in an anatomy, comprising:

obtaining plural image data, representative of plural images of a same portion of the anatomy, derived from at least two imaging modalities selected from the group consisting of magnetic resonance imaging, x-ray imaging, and ultrasound imaging;

identifying from the plural image data a possible lesion in said plural images;

extracting, for each of said plural images derived from said at least two imaging modalities, at least one feature related to characterization of a lesion from image data corresponding to the identified possible lesion; and merging in a common image classifier a plurality of extracted features, including at least one feature related to characterization of a lesion from each of said plural images derived from said at least two imaging modalities to characterize said possible lesion based on the merged plurality of extracted features and yield a corresponding classification.

2. The method according to claim 1, further comprising:

extracting features from at least one of the interior or the surface of the identified possible lesion.

3. The method according to claim 1, further comprising:

extracting geometric based features of the identified possible lesion.

4. The method according to claim 3, further comprising:

extracting at least one of circularity and irregularity geometric based features of the identified possible lesion.

5. The method according to claim 4, further comprising:
extracting the circularity geometric based features of the identified possible lesion based on the following equation:

$$C = \frac{EFV}{V}$$

where C is a measure of circularity of the identified possible lesion, EFV is an effective volume of the identified possible lesion, and V is a sphere having a same volume as the effective volume of the identified possible lesion.

6. The method according to claim 4, further comprising:
extracting the irregularity geometric based features of the identified possible lesion based on the following equation:

$$I = 1 - \pi \cdot \frac{(ED)^2}{S}$$

where I is a measure of irregularity of the lesion, ED is an effective diameter of the identified possible lesion, and S is a surface area of the identified possible lesion.

7. The method according to claim 1, further comprising:
extracting gray level based features of the identified possible lesion.

8. The method according to claim 1, further comprising:
extracting from each of said images derived from said at least two modalities gradient based features of the identified possible lesion.

9. The method according to claim 1, further comprising:
extracting from each of said images derived from said at least two modalities gradient based features of the identified possible lesion based on at least one of the following equations:

$$GF1 = \sum_{i \in lesion} \frac{R_i \cdot G_i}{G_i}$$

$$GF2 = \sum_{i \in shell} \frac{R_i \cdot G_i}{G_i}$$

where GF1 and GF2 are a gradient based features of the identified possible lesion, and a 3-voxel thick shell around the identified possible lesion, respectively, $R_i$ is an effective diameter of the lesion, and $G_i$ is a surface area of the identified possible lesion.

10. The method according to claim 1, further comprising:
extracting from each of said images derived from said at least two modalities a texture based feature of the identified possible lesion.

11. The method according to claim 10, further comprising:
extracting from each of said images derived from said at least two modalities the texture based feature based on the following equation:

T=rms {F(lesion)} where T is a texture based feature of the lesion, and F is a Fourier transform of the voxel values within the lesion.

12. The method according to anyone of claim 1, further comprising:
extracting and comparing features of the identified possible lesion with features of a surrounding area of the identified possible lesion for each of said images derived from said at least two different modalities.

13. The method according to anyone of claim 1, wherein said extracting step comprises:
extracting from each of said images derived from said at least two different modalities temporal based features including at least one of Gd-DTPA uptake, speed of Gd-DTPA uptake, and inhomogeneity of Gd-DTPA uptake in the lesion calculated in terms of volume, uptake in the center of lesion, uptake in the margin of the lesion, a flow of contrast agent into the lesion, and a flow of contrast agent out of the lesion.

14. The method according to anyone of claim 13, wherein said characterizing step comprises:
providing at least one of a probability of malignancy, diagnosis, and prognosis of the identified possible lesion based on the extracted features.

15. The method according to anyone of claim 13, wherein said characterizing step comprises:
using an artificial neural network to provide at least one of a probability of malignancy, diagnosis, and prognosis of the identified possible lesion based on the at least one feature extracted from the plural images derived from said at least two imaging modalities.

16. The method according to claim 1, wherein said characterizing step comprises:
providing at least one of a probability of malignancy, diagnosis, and prognosis of the identified possible lesion based on the extracted features.

17. The method according to claim 1, wherein said characterizing step comprises:
using an artificial neural network to provide at least one of a probability of malignancy, diagnosis, and prognosis of the identified possible lesion based on the at least one feature extracted from the plural images derived from said at least two imaging modalities.

18. The method according to anyone of claim 1, further comprising:
extracting features that characterize a lesion within the image data in at least one of two dimensions and three dimensions.

19. A method for the analysis of a lesion in an anatomy, comprising:
obtaining plural image data, representative of plural images of a same portion of the anatomy, derived from at least one imaging modality selected from the group consisting of magnetic resonance imaging, x-ray imaging, and ultrasound imaging, said plural images derived at different times during introduction of a contrast agent into said anatomy;
identifying from the image data a possible lesion in said plural images;
extracting at least one feature related to inhomogeneity of uptake of a lesion from said plural image data corresponding to the identified possible lesion ; and
characterizing said possible lesion based at least in part on the at least one feature extracted from the plural images derived from said at least one imaging modality.

20. The method according to claim 19, further comprising:
extracting geometric based features of the identified possible lesion; and
characterizing said possible lesion based at least in part on the extracted geometric based features.

21. The method according to claim 20, further comprising:
extracting at least one of circularity and irregularity geometric based features from the identified possible lesion.

22. The method according to claim 19, further comprising:
extracting gray level based features from the identified possible lesion; and
characterizing said possible lesion based at least in part on the extracted gray level based features.

23. The method according to claim 19, further comprising:
extracting from each of said images gradient based features of the identified possible lesion; and
characterizing said possible lesion based at least in part on the extracted gradient based features.

24. The method according to claim 19, further comprising:
extracting from each of said images a texture based feature of the identified possible lesion; and
characterizing said possible lesion based at least in part on the extracted texture based features.

25. The method according to claim 19, further comprising:
extracting and comparing features of the identified possible lesion with features of a surrounding area of the identified possible lesion for each of said images; and
characterizing said possible lesion based at least in part on the extracted and compared features.

26. The method according to claim 19, wherein said determining step comprises:
determining from each of said images a variation over time of at least one of Gd-DTPA uptake, speed of Gd-DTPA uptake, and inhomogeneity of Gd-DTPA uptake in the lesion calculated in terms of volume, uptake in the center of lesion, uptake in the margin of the lesion, a flow of contrast agent into the lesion, and a flow of contrast agent out of the lesion.

27. The method according to claim 26, wherein said characterizing step comprises:
providing at least one of a probability of malignancy, diagnosis, and prognosis of the identified possible lesion based on the extracted features.

28. The method according to claim 26, wherein said characterizing step comprises:
using an artificial neural network to provide at least one of a probability of malignancy, diagnosis, and prognosis of the identified possible lesion based on the at least one feature extracted from the plural images.

29. The method according to claim 19, wherein said characterizing step comprises:
providing at least one of a probability of malignancy, diagnosis, and prognosis of the identified possible lesion based on the extracted features.

30. The method according to claim 19, wherein said characterizing step comprises:
using an artificial neural network to provide at least one of a probability of malignancy, diagnosis, and prognosis of the identified possible lesion based on the at least one feature extracted from the plural images.

31. The method according to claim 19, further comprising:
extracting features that characterize a lesion within the image data in at least one of two dimensions and three dimensions.

32. A storage medium storing a program for performing the steps recited in one of claims 1–31.

33. The method according to claim 19, wherein said extracting step comprises extracting a feature related to a time variation in a voxel value of the lesion.

34. The method according to claim 19, wherein said extracting step comprises extracting a feature related to a time variation in a standard deviation of a voxel value in the lesion.

35. The method according to claim 19, wherein said extracting step comprises extracting a feature related to a radial gradient frequency variation in the lesion.

36. The method according to claim 19, wherein:
said extracting step comprises extracting from said plural image data corresponding to the identified possible lesion at least one further feature related to an uptake of a lesion;
and said characterizing step comprises characterizing said possible lesion based at least in part on the one further feature related to the uptake of the lesion.

37. The method according to claim 36, wherein said extracting step comprises extracting a feature related to uptake in a margin of the lesion.

38. The method according to claim 36, wherein said extracting step comprises extracting a feature related to uptake in a center of the lesion.

39. The method according to claim 36, wherein said extracting step comprises extracting a feature related to a speed of uptake in the lesion.

40. The method according to claim 19, wherein:
said extracting step comprises extracting at least one further feature related to a spatial characteristic of a lesion from said plural image data corresponding to the identified possible lesion;
said characterizing step comprises characterizing said possible lesion based at least in part on the one further feature related to the spatial characteristic of the lesion.

41. The method according to claim 40, wherein said extracting step comprises extracting a feature related to a textural characteristic of the lesion.

42. The method according to claim 40, wherein said extracting step comprises extracting a feature related to a power spectrum of voxel values in the lesion.

43. The method according to claim 40, wherein said extracting step comprises extracting a feature related to a variation in a margin characteristic of the lesion.

44. The method according to claim 40, wherein said extracting step comprises extracting a feature related to a radial gradient index of the lesion.

45. The method according to claim 40, wherein said extracting step comprises extracting a feature related to a margin gradient of the lesion.

46. The method according to claim 40, wherein said extracting step comprises extracting a feature related to a shape feature of the lesion.

47. The method according to claim 46, wherein said extracting step comprises extracting a feature related to an irregularity of the lesion.

48. The method according to claim 46, wherein said extracting step comprises extracting a feature related to a circularity of the lesion.

49. A system for the analysis of a lesion in an anatomy, comprising:
means for obtaining plural image data, representative of plural images of a same portion of the anatomy, derived from at least two imaging modalities selected from the group consisting of magnetic resonance imaging, x-ray imaging, and ultrasound imaging;

means for identifying from the image data a possible lesion in said plural images;

means for extracting, for each of said plural images derived from said at least two imaging modalities, at least one feature related to characterization of a lesion from said plural image data corresponding to the identified possible lesion; and means for merging in a common image classifier a plurality of extracted features, including at least one feature extracted from each of the plural images derived from said at least two imaging modalities to characterize said possible lesion based on the merged extracted features and yield a corresponding classification.

50. A system for the analysis of a lesion in an anatomy, comprising:

means for obtaining plural image data, representative of plural images of a same portion of the anatomy, derived from at least one imaging modality selected from the group consisting of magnetic resonance imaging, x-ray imaging and ultrasound imaging, said plural images derived at different times during introduction of a contrast agent into said anatomy;

means for identifying from the image data a possible lesion in said plural images;

means for extracting at least one feature related to inhomogeneity of uptake of a lesion from said image data corresponding to the identified possible lesion;

and means for characterizing said possible lesion based at least in part on the at least one feature extracted from the plural images derived from said at least one imaging modality.

51. A method for the analysis of a lesion in an anatomy, comprising:

obtaining plural image data, representative of plural images of a same portion of the anatomy, derived from at least one imaging modality selected from the group consisting of magnetic resonance imaging, x-ray imaging, and ultrasound imaging;

identifying from the image data a possible lesion in said plural images;

extracting a radial gradient peak distinction and a variance of a gradient along a margin of said possible lesion; and characterizing said possible lesion based at least in part on said radial gradient peak distinction and said variance of a gradient along a margin extracted from the plural images derived from said at least one imaging modality.

* * * * *